US011657311B2

(12) United States Patent
Kovacs

(10) Patent No.: US 11,657,311 B2
(45) Date of Patent: May 23, 2023

(54) LINK PREDICTION BASED ON 3-STEP CONNECTIVITY

(71) Applicant: Northeastern University, Boston, MA (US)

(72) Inventor: Istvan Kovacs, Brighton, MA (US)

(73) Assignee: Northeastern University, Boston, MA (US)

( * ) Notice: Subject to any disclaimer, the term of this patent is extended or adjusted under 35 U.S.C. 154(b) by 1298 days.

(21) Appl. No.: 15/985,023

(22) Filed: May 21, 2018

(65) Prior Publication Data

US 2018/0349786 A1    Dec. 6, 2018

Related U.S. Application Data

(60) Provisional application No. 62/513,926, filed on Jun. 1, 2017, provisional application No. 62/548,454, filed on Aug. 22, 2017.

(51) Int. Cl.
*G06N 7/01* (2023.01)
*G06Q 30/0601* (2023.01)
*G16H 50/20* (2018.01)
*G16B 30/00* (2019.01)
*G16B 5/20* (2019.01)

(Continued)

(52) U.S. Cl.
CPC ............... *G06N 7/01* (2023.01); *G06N 5/022* (2013.01); *G06Q 30/0631* (2013.01); *G16B 5/20* (2019.02); *G16B 30/00* (2019.02); *G16H 20/10* (2018.01); *G16H 50/20* (2018.01); *G16B 20/00* (2019.02)

(58) Field of Classification Search
CPC ..................................................... G06N 3/049
See application file for complete search history.

(56) References Cited

U.S. PATENT DOCUMENTS 9,294,497 B1 *   3/2016   Ben-Or ............... H04L 63/1433
2007/0038385 A1 *   2/2007   Nikolskaya ............ G16B 50/20
702/19

(Continued)

OTHER PUBLICATIONS

Adamic et al., "Friends and Neighbors on the Web," Social Networks 25, pp. 211-230 (2003).

(Continued)

*Primary Examiner* — Michael J Huntley
*Assistant Examiner* — Peter D Coughlan
(74) *Attorney, Agent, or Firm* — Hamilton, Brook, Smith & Reynolds, P.C.

(57) ABSTRACT

A method and corresponding system identify missing interactions in incompletely known datasets represented as complex networks. The method identifies missing connections in a complex network. The method accesses an electronic representation of the network. The network includes nodes and links, the nodes represent entities, and the links represent interactions between the entities. For each pair of nodes not directly connected by a link, the method determines a number of paths connecting the pair of nodes and calculates a prediction score for the pair of nodes based on the number of paths connecting the pair of nodes. The method ranks the pairs of nodes based on the prediction scores, resulting in an ordered list of node pairs, and selects at least a subset of the pairs of nodes based on the ordered list of node pairs. The selected pairs of nodes represent missing connections in the network.

30 Claims, 19 Drawing Sheets

(51) Int. Cl.
  *G06N 5/022* (2023.01)
  *G16H 20/10* (2018.01)
  *G16B 20/00* (2019.01)

(56) References Cited

U.S. PATENT DOCUMENTS

| | | | | |
|---|---|---|---|---|
| 2011/0152115 | A1* | 6/2011 | Staudt | C12Q 1/6886 |
| | | | | 506/9 |
| 2013/0144818 | A1* | 6/2013 | Jebara | G06Q 50/00 |
| | | | | 706/12 |
| 2016/0217056 | A1* | 7/2016 | Chua | G06F 11/3452 |
| 2017/0369945 | A1* | 12/2017 | Li | G09B 19/00 |
| 2018/0089318 | A1* | 3/2018 | Chatterjee | H04L 67/306 |
| 2019/0130290 | A1* | 5/2019 | Kerber | G06N 5/022 |

OTHER PUBLICATIONS

Albert et al., "Diameter of the world wide web," Nature, vol. 401, pp. 130-131 (Sep. 9, 1999).
Ashburner M, et al., "Gene ontology: tool for the unification of biology," Nature genetics, vol. 25, pp. 25-29. (May 2000).
*Arabidopsis* Interactome Mapping Consortium, "Evidence for Network Evolution in an *Arabidopsis* Interactome Map.," Science, vol. 333, 6042, pp. 601-607 (Jul. 29, 2011).
Barabási et al., "Evolution of the social network of scientific collaborations,". Physica A, 311(3-4), pp. 590-614 (Jan. 16, 2002).
Barabáasi et al., "Network medicine: a network-based approach to human disease," Nature Reviews Genetics 12, pp. 56-68 (Jan. 2011).
Barabási et al., "Emergence of scaling in random networks," Science, vol. 286, pp. 509-512 (Oct. 15, 1999).
Brun, C. et al., "Functional classification of proteins for the prediction of cellular function from a protein-protein interaction network," Genome biology, vol. 5, Issue I, Article R6, pp. R6.1-R6.13 (Dec. 15, 2003).
Cannistraci et al., "From link-prediction in brain connectors and protein interactomes to the local-community-paradigm in complex networks," Sci. Rep 3, 1613 (Apr. 8, 2013).
Chua et al., "Exploiting indirect neighbours and topological weight to predict protein function from protein-protein interactions," Bioinformatics, vol. 22, No. 13, pp. 1623-1630 (Advance Access Publication Apr. 21, 2006).
Clauset, et al., "Hierarchical structure and the prediction of missing links in networks," Nature, vol. 453, pp. 98-101 (May 2008).
Csermely, P. "Weak links: the universal key to the stabilitv of networks and complex systems," Springer, Berlin; London (2009).
Dehal, et al., "Two Rounds of Whole Genome Duplication in the Ancestral Vertebrate," PLoS Biol 3(10), Issue e314, pp. 1700-1708 (Oct. 2005).
Di Gioia et al., "Interactome analysis reveals that FAM161A, deficient in recessive retinitis pigmentosa, is a component of the Golgi-centrosomal network," Human Molecular Genetics, vol. 24, No. 12, pp. 3359-3371 (Mar. 5, 2015).
Feldman et al., "Network properties of genes harboring inherited disease mutations," Proceedings of the National Academy of Sciences, vol. 105, No. 11, pp. 4323-4328. (Mar. 18, 2008).
The GOA database: Gene Ontology annotation updates for 2015, Nucleic Acids Res. 2015, vol. 43 (Database issue):D1049-56. http://www.ebi.ac.uk/GOA Version: Dec. 7, 2015; gene association. goa human, pp. D1057-D1063, published online Nov. 6, 2014.
Ghiassian et al., "A DIseAse MOdule Detection (DIAMOnD) Algorithm Derived from a Systematic Analysis of Connectivity Patterns of Disease Proteins in the Human Interactome," PLoS Computational Biology pcbi.1004120, pp. 1/21-21/21 (Apr. 8, 2015).
Gibson et al., "Improving evolutionary models of protein interaction networks," Bioinformatics, vol. 27, No. 3, p. 376-382 (Nov. 9, 2010).

Goh KI, et al., "The human disease network," Proceedings of the National Academy of Sciences, vol. 104, No. 21, pp. 8685-8690. (May 22, 2007).
Goldberg et al., "Assessing experimentally derived interactions in a small world," Proceedings of the National Academy of Sciences, vol. 100, No. 8, pp. 4372-4376. (Apr. 15, 2003).
Granovetter, M., "The Strength of Weak Ties," American Journal of Sociology, vol. 78, Issue 6, pp. 1360-1380. (May 1973).
Gray et al., "Genenames.org: the HGNC resources in 2015," Nucleic Acids Res. 2015, vol. 43 (Database issue):D1079-85. http://www.genenames.org/, pp. D1079-D1085, published online Oct. 31, 2014.
Guimera et al., "Missing and spurious interactions and the reconstruction of complex networks," Proc. Natl. Acad. Sci. USA, vol. 106, No. 52, pp. 22073-22078 (Dec. 29, 2009).
Guney et al., "Network-based in silico drug efficacy screening," Nature Communications 7:10331, pp. 1-13 (Feb. 1, 2016).
Han et al., "Effect of sampling on topology predictions of protein-protein interaction networks," Nature Biotechnology. Vol. 23, No. 7, pp. 839-844 (Jul. 7, 2005).
Hanley et al., "The meaning and use of the area under a receiver operating characteristic (ROC) curve," Radiology 143, pp. 29-36 (Apr. 1982).
Hart et al., "How complete are current yeast and human protein-interaction networks," Genome Biol., vol. 7, Issue 11, Article I20, pp. I20.2-I20.9 (Dec. 1, 2006).
Hein MY et al., "A Human Interactome in Three Quantitative Dimensions Organized by Stoichiometries and Abundances," Cell 163, pp. 712-723 (Oct. 22, 2015).
Herlocker et al., "Evaluating collaborative Filtering recommender systems," ACM T. Inform. Syst., vol. 22, No. 1, pp. 5-53, (Jan. 1, 2004).
Huttlin et al., "The BioPlex Network: A Systematic Exploration of the Human Interactome," Cell 162, pp. 425-440 (Jul. 16, 2015).
Ideker et al., "Protein networks in disease," Genome research 18, pp. 644-652. (2008), Downloaded from the Internet on Feb. 27, 2022 at https://www.genome.cship.org.
Ispolatov et al., "Binding properties and evolution of homomers in protein-protein interaction networks," Nucleic Acids Res., 2005, vol. 33, No. 11, pp. 3629-3635. (Jun. 27, 2005).
Jaccard P, "The distribution of or the Flora in the alpme zone," The New Phytologist, vol. 11, No. 2, pp. 37-50. (Feb. 29, 1912).
Jimenez-Sanchez et al., "Human disease genes," Nature, vol. 409, pp. 853-855. (Feb. 15, 2001).
Keskin et al., "Predicting Protein-Protein Interactions from the Molecular to the Proteome Level. Chemical," Reviews 116, pp. 4884-4909 (Apr. 13, 2016).
Kovács et al., "A unified data representation theory for network visualization, ordering and coarse-graining," Scientific Reports (Nature) 5:13786, pp. 1-10 (Sep. 8, 2015).
Krapivsky et al., "Network growth by copying," Phys. Rev. E 71, 036118, pp. 036118-1-036118-7 (Mar. 17, 2005).
Kuchaiev et al., "Geometric de-noising of protein-protein interaction networks," PloS Comput. Biol., vol. 5. Issue 8, e1000454 (Aug. 7, 2009).
Liben-Nowell et al., "The Link-Prediction Problem for Social Networks," J. Am. Soc. Inf. Sci. Tec. 58, 1019-1031 (Jan. 8, 2004).
López-Bigas et al., "Genome-wide identification of genes likely to be involved in human genetic disease,". Nucleic acids research, vol. 32, No. 10, pp. 3108-3114. (Jun. 4, 2004).
Liu et al., "Complex discovery from weighted PPI networks," Bioinformatics, vol. 25, No. 15, pp. 1891-1897 (May 12, 2009).
Liu et al., "Correlations between community structure and link formation in complex networks," PLoS One, vol. 8, Issue 9, e72908 (Sep. 6, 2013).
Lü et al.. "Link prediction in complex networks: A survey," Physica A 390, 2011, pp. 1150-1170 (available online Dec. 2, 2010).
Lü et al., "Similarity index based on local paths for link prediction of complex networks," Phys. Rev. E 80, 046122, pp. 046122-046122-9 (Oct. 26, 2009).
Lü et al.. "Toward link predictability of complex networks," Proc. Natl. Acad. Sci. USA, vol. 112, No. 8, pp. 2325-2330 (Feb. 24, 2015).

(56) References Cited

OTHER PUBLICATIONS

Luck et al., "Proteome-Scale Human Interactomics," Trends in Biochemical Sciences, vol. 42, No. 5, pp. 342-354 (May 2017).
Magger et al., "Enhancing the prioritization of disease-causing genes through tissue specific protein interaction networks," PLoS computational biology, vol. 8, Issue 9, e1002690. (Sep. 27, 2012).
Menche et al., "Uncovering disease-disease relationships through the incomplete interactome," Science, vol. 347, Issue 6224, pp. 1257601-1-1257601-8 (Feb. 20, 2015).
Mestres et al., "Data completeness—the Achilles heel of drug-target networks," Nature biotechnology, vol. 26. No. 9, pp. 983-984. (Sep. 2008).
Molloy et al., "A Critical Point for Random Graphs with a Given Degree Sequence," Random Structures and Algorithms. Random Struct. Algorithms 6 161-180 (Aug. 14, 2000).
Mosca et al., "Towards a detailed atlas of protein-protein interactions," Current opinion in structural biology 23, pp. 929-940 (Jul. 26, 2013).
Mosca et al., "Interactome3D: adding structural details to protein networks," Nature Methods, vol. 10, No. 1, pp. 47-53 (Jan. 2013).
Newman et al., "Clustering and preferential attachment in growing networks," Phys Rev E, vol. 64, 025102(R), pp. 025102-1-025102-4 (Jul. 26, 2001).
Ouedraogo et al., "The Duplicated Genes Database: Identification and Functional Annotation of Co-Localised Duplicated Genes across Genomes," PLoS One, vol. 7, Issue 11, e50653. (Nov. 28, 2012).
Parmeggiani F, Editorial, "Clinics, Epidemiology and Genetics of Retinitis Pigmentosa," Current Genomics, vol. 12, No. 4, pp. 236-237. (2011).
Peng et al., "Link Prediction in Social Networks: the State-of-the-Art," Science China: Information Sciences vol. 58, 011101:1-011101:38 (Jan. 2015).
Peterson et al., "Simulated Evolution of Protein-Protein Interaction Networks with Realistic Topology," PLoS One, vol. 7, Issue 6, e39052 (Jun. 29, 2012).
Pinkert et al., "Protein Interaction Networks—More Than Mere Modules," PLoS Comput . . . Biol., vol. 6, Issue 1, e1000659. doi:10.1371/journal.pcbi.1000659 (Jan. 29, 2010).
Pržulj et al., "Functional topology in a network of protein interactions," Bioinformatics, vol. 20, No. 3, 2004, pp. 340-348 (accepted Aug. 6, 2003).
Pržulj et al., "Modelling protein-protein interaction via a stickiness index," J. R. Soc. Interface 3, 711-716 (Aug. 22, 2006).
Ramos et al., "Phenotype-genotype integrator (PheGenI): synthesizing genome-wide association study (GWAS) data with existing genomic resources," European Journal of Human Genetics (2014), 22, pp. 144-147 (May 22, 2013).
Ravasz et al., "Hierarchical organization of modularity in metabolic networks," Science, vol. 297, pp. 1551-1555 (Aug. 30, 2002).
Reverter et al., "Mining tissue specificity, gene connectivity and disease association to reveal a set of genes that modify the action of disease causing genes," BioData Mining 1:8. (Sep. 19, 2008).
Rolland et al., "A protcome-scale map of the human interactome network," Cell 159:5, pp. 1212-1226 (Nov. 20, 2014).
Rual et al., "Towards a proteome-scale map of the human protein-protein interaction network," Nature, vol. 437, pp. 1173-1178. (Oct. 20, 2005).
Sahni et al., "Widespread Macromolecular Interaction Perturbations in Human Genetic Disorders," Cell, vol. 161, Issue 3, pp. 647-660 (Apr. 23, 2015).
Saito et al., "Interaction generality, a measurement to assess the reliability of a protein-protein interaction," Nucleic acids research, 2002, vol. 30, No. 5, pp. 1163-1168 (Jan. 2, 2002).
Solé et al., "A model of large-scale proteome evolution," Adv. Comp. Syst. 5:43 (Jul. 12, 2002).
Stark et al., "BioGRID: a General Repository for Interaction Datasets," Nucleic Acids Res., Jan. 1, 2006; vol. 34, pp. D535-D539, BioGRID Release 3.4.143 (Oct. 17, 2005).
Stelzl et al., "A human protein-protein interaction network: a resource for annotating the proteome," Cell, vol. 122 pp. 957-968 (Sep. 23, 2005).
Tan et al., "Link Prediction in Complex Networks: A Mutual Information Perspective," PLoS One, vol. 9, Issue 9, e 107056 (Sep. 10, 2014).
Vazquez, Chapter 8, "Protein Interaction Networks," Neuroproteomics, editor: Alzate, O. Boca Raton (FL): CRC Press/Taylor & Francis; (2010).
Vazquez et al., "Modeling of Protein Interaction Networks," ComPlexUs 1:38-44; (Oct. 26, 2018).
Vidal, "How much of the human protein interactome remains to be mapped?" Science Signaling, vol. 9, Issue 427, eg7. (May 10, 2016).
Vidal et al, "The human proteome—a scientific opportunity for transforming diagnostics, therapeutics, and healthcare," Clinical Proteomics. 9:6. (2012).
Wang et al., "Global Edgetic Rewiring in Cancer Networks," Cell Systems 1, pp. 251-253 (Oct. 28, 2015).
Wang et al., "A Theoretical Analysis of Normalized Discounted Cumulative Gain (NDCG) Ranking Measures," In Proceedings of the 26th Annual Conference on Learning Theory (COLT 2013).
Wang et al., "CD-Based Indices for Link Prediction in Complex Network," PLoS One 11(1), C0146727, pp. 1/13-13/13 (Jan. 11, 2016).
Yan et al., "Finding missing edges in networks based on their community structure," Phy. Rev. E 85, pp. 056112-1-056112-6 (May 15, 2012).
Yang et al., "Predicting missing links in complex networks based on common neighbors and distance," Sci. Rep. 6: 38208 (Dec. 1, 2016).
You et al., "Using manifold embedding for assessing and predicting protein interactions from high-throughput experimental data," Bioinformatics (Oxford, England), vol. 26, No. 21, pp. 2744-2751 (Sep. 3, 2010).
Yu et al., "High Quality Binary Protein Interaction Map of the Yeast Interactome Network,". Science, vol. 322, pp. 104-110 (Oct. 3, 2008).
Zanzoni et al., "A network medicine approach to human disease," FEBS letters 583, pp. 1759-1765 (Mar. 6, 2009).
Zhang, "Evolution by gene duplication: an update," Trends in Ecology & Evolution, vol. 18, No. 6, pp. 292-298 (Jun. 2003).
Zhang et al., "The reconstruction of complex networks with community structure," Sci. Rep. 5, 17287 (Dec. 1, 2015).
Zhou et al., Predicting missing links via local information, Eur. Phys. J. B 71, pp. 623-630 (Jun. 1, 2009).
Zhu et al., "An information-theoretic model for link prediction in complex networks," Sci. Rep. 5, 13707 (Sep. 3, 2015).

* cited by examiner

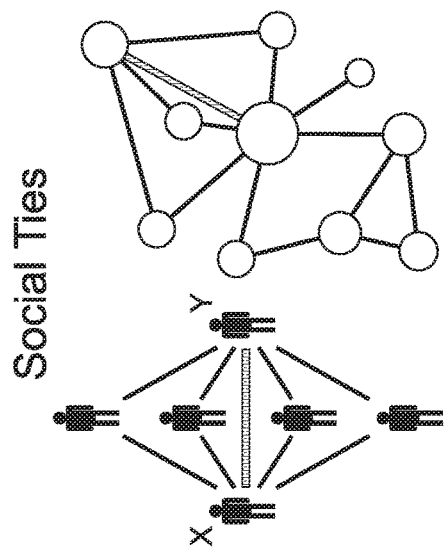
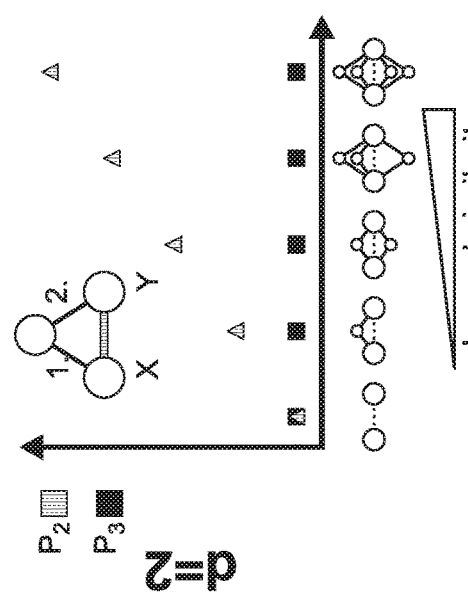
Fig. 2A
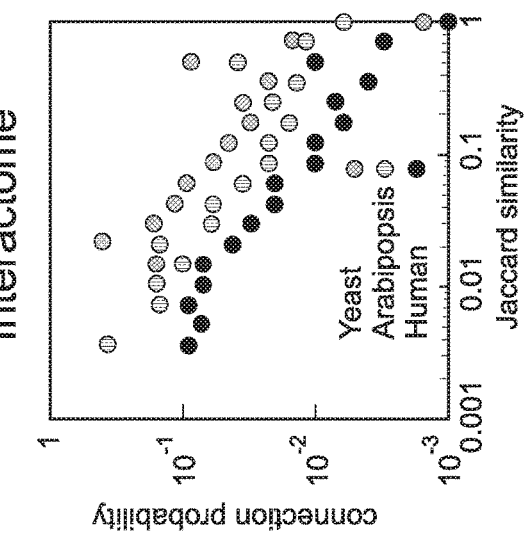
Fig. 2B
Fig. 2C

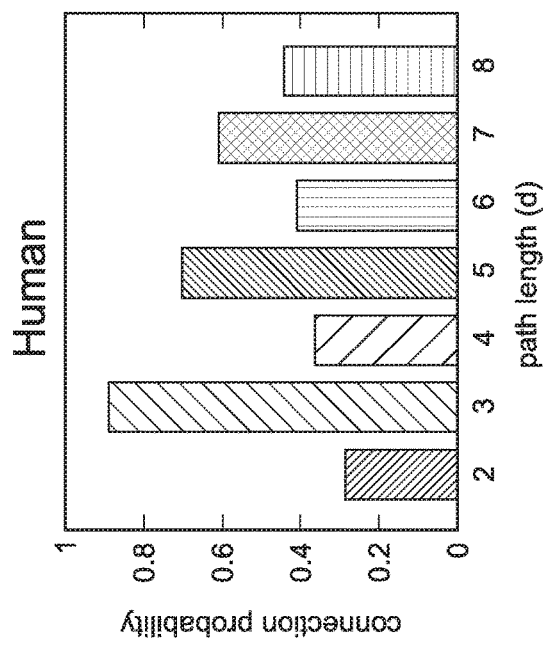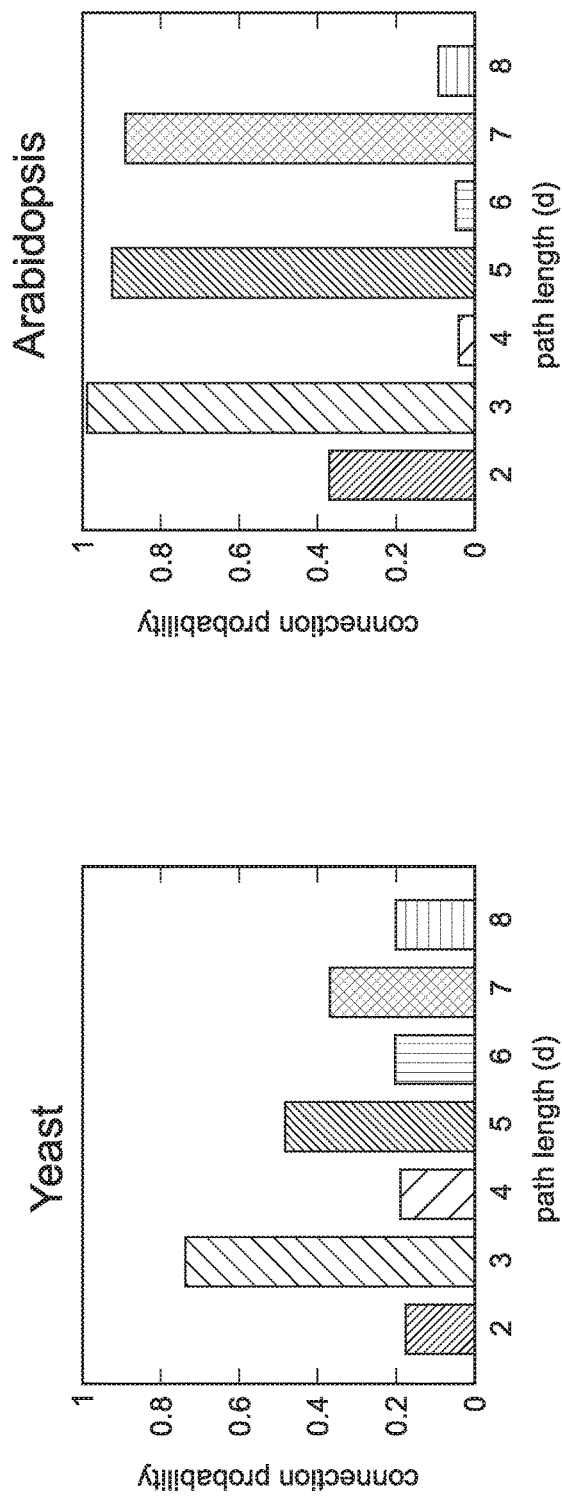

PROTEIN STRUCTURE

Self-interacting Interface

Complementary Interfaces

Complementary Interfaces

GENE DUPLICATION homomers heteromers

Duplication + Incompleteness cliques bipartile

Link Prediction

In Silico

High-throughput

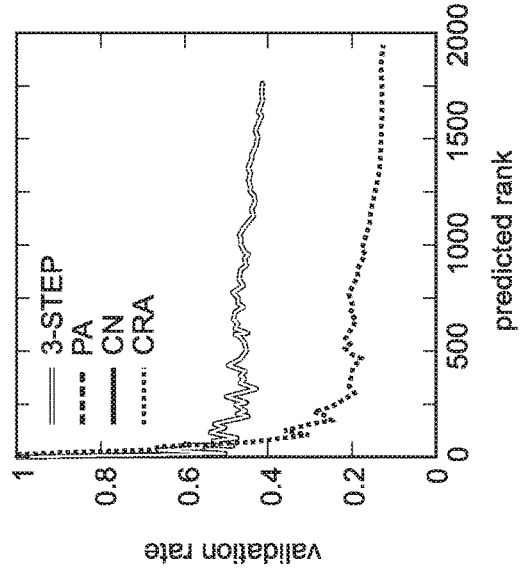
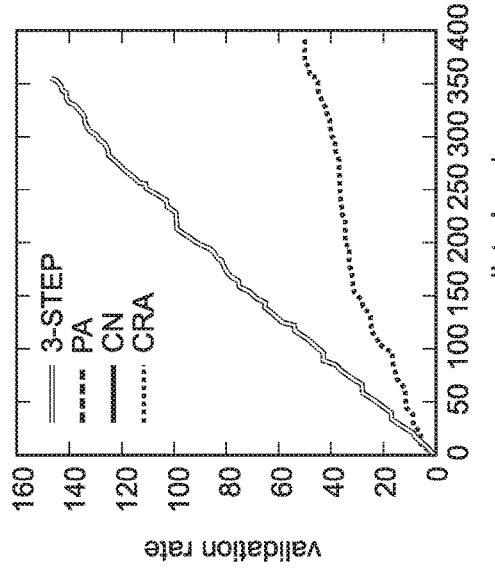
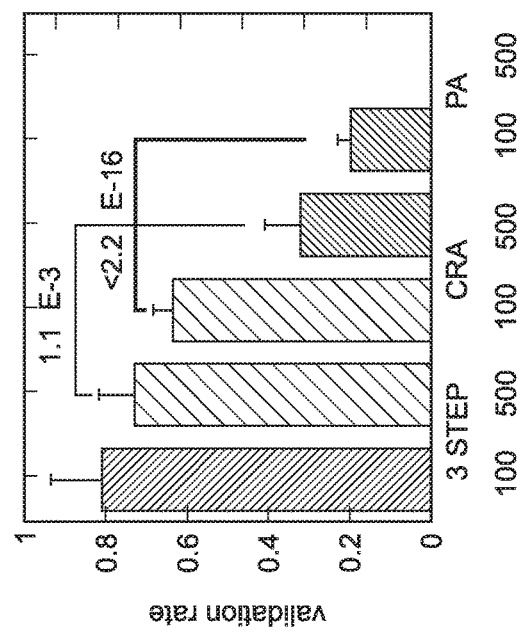
Fig. 5G
Fig. 5H
Fig. 5I

Retinitis Pigmentosa

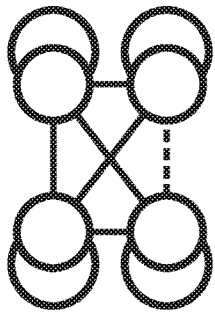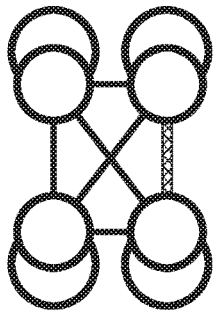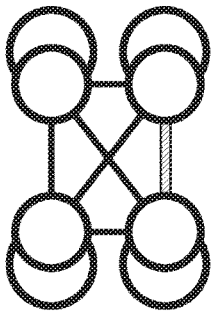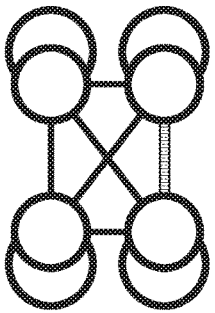
Fig. 7D  
INCOMPLETENESS
Fig. 7E  
PA
Fig. 7F  
CN
Fig. 7G  
3-STEP
LINK PREDICTION

US 11,657,311 B2

LINK PREDICTION BASED ON 3-STEP CONNECTIVITY

RELATED APPLICATIONS

This application claims the benefit of U.S. Provisional Application No. 62/513,926, filed on Jun. 1, 2017, and U.S. Provisional Application No. 62/548,454, filed on Aug. 22, 2017. The entire teachings of the above applications are incorporated herein by reference.

GOVERNMENT SUPPORT

This invention was made with government support under P50HG004233 from National Institutes of Health, National Human Genome Research Institute Center of Excellence in Genome Science. The government has certain rights in the invention.

BACKGROUND

Network-based link prediction has a long history in social networks, providing a large arsenal of graph-based methods, routinely applied for social, biological, and technological networks as well. Most of these tools are either explicitly or implicitly based on the triadic closure principle (TCP), stating that similar nodes (sharing many of their neighbors) are likely to be connected. The TCP, however, has only limited applicability, unable to find important missing interactions, while predicting a large number of connections where there is no interaction in reality.

SUMMARY

Described herein are methods and systems that identify missing interactions in incompletely known datasets represented as complex networks. One example embodiment is a method of identifying missing connections in a complex network. The example method includes accessing an electronic representation of the network. The network includes nodes and links, the nodes represent entities, and the links represent interactions between the entities. The method further includes, for each pair of nodes in the network not directly connected by a link, (i) determining a number of paths connecting the pair of nodes, where each path is a length of at least three connections spanning between the pair of nodes in the network, and (ii) calculating a prediction score for the pair of nodes based on the number of paths connecting the pair of nodes. The method further includes ranking the pairs of nodes based on the prediction scores, resulting in an ordered list of node pairs, and selecting at least a subset of the pairs of nodes based on the ordered list of node pairs. The selected pairs of nodes represent missing connections in the network.

Another example embodiment is a system for identifying missing connections in a complex network. The system includes memory and a processor in communication with the memory. The memory stores an electronic representation of a network. The network includes nodes representing entities and links between nodes representing interactions between corresponding entities. The processor is configured to, for each pair of nodes in the network not directly connected, (i) determine a number of paths connecting the pair of nodes, where each path is a length of at least three connections spanning between the pair of nodes in the network, and (ii) calculate a prediction score for the pair of nodes based on the number of paths connecting the pair of nodes. The processor is further configured to rank the pairs of nodes based on the prediction scores, resulting in an ordered list of node pairs, and select at least a subset of the pairs of nodes based on the ordered list of node pairs. The selected pairs of nodes represent missing connections in the network.

The missing connections can be communicated to at least a portion of entities represented by the selected pairs of nodes. Connections can be created in the network between each of the selected pairs of nodes. In some embodiments, data can be collected regarding interactions among a plurality of entities, and the electronic representation of the network can be created from the collected data, where nodes in the network represent the entities, and connections between nodes in the network represent interactions between corresponding entities.

In some embodiments, a statistical significance can be calculated for each selected pair of nodes by comparing a connection between each pair of nodes to a pool of randomized networks with the same node degrees. In some embodiments calculating a prediction score for a pair of nodes can include calculating the prediction score based on the number of paths connecting the pair of nodes and a geometric mean of degrees of intermediate nodes between the pair of nodes.

In some embodiments, probabilities of existence of connections between the pairs of nodes can be estimated by, for each pair of nodes (i) performing a leave-one-out analysis, wherein a direct connection between the pair of nodes is left out of the network and each of the pair of nodes is scored in a context of a representation of the remaining network, (ii) adding the leave-one-out score of each of the pair of nodes to the ordered list of node pairs, (iii) estimating a probability of existence of a connection between the pairs of nodes based on the ordered list of node pairs, and (iv) assigning the estimated probability to the pair of nodes.

The network can be a social network, where the nodes of the network represent real-life individuals, and the connections between nodes in the network represent relationships between corresponding individuals. In such embodiments, the selected pairs of nodes can represent relationship recommendations between pairs of corresponding real-life individuals, and the relationship recommendations can be communicated to the individuals represented by the selected pairs of nodes. A connection between a pair of nodes can be created if at least one of the individuals represented by the nodes verifies a relationship between the individuals.

The network can be a protein network, where the nodes of the network represent real-life human proteins, and the connections between nodes in the network represent functional associations between corresponding proteins. In such embodiments, the selected pairs of nodes can represent new functional relationships between pairs of corresponding proteins. In such embodiments a protein sequence can be obtained from a patient and applied to the network to determine at least one of a disease afflicting the patient, a drug to use for treating the patient, and a potential reaction by the patient to a drug.

The network can be a professional network, where the nodes of the network represent real-life individuals and businesses, and the connections between nodes in the network represent employment relationships between corresponding individuals and companies. In such embodiments, the selected pairs of nodes can represent employment recommendations between corresponding individuals and companies, and the employment recommendations can be communicated to the individuals or companies represented by the selected pairs of nodes.

The network can represent real-life individuals and products, and the connections between nodes in the network can represent purchases of corresponding products by corresponding individuals. In such embodiments, the selected pairs of nodes can represent purchase recommendations between corresponding individuals and products. The purchase recommendations can be communicated to individuals represented by the selected pairs of nodes, and a connection can be created between a pair of nodes if the individual represented by the pair of nodes purchases a product represented by the pair of nodes.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIGS. 2A-2I are graphs illustrating example paths of various lengths and connectivity.

FIGS. 5A-5L are graphs illustrating example computational and experimental validation of an example embodiment involving the human interactome.

FIGS. 7A-7G are graphs illustrating a simplified example of gene duplication and link prediction.

DETAILED DESCRIPTION

A description of example embodiments follows.

Disclosed herein are 3-step link prediction (3SLP) methods and systems. As a case study of interest, 3SLP was validated for physical protein-protein interaction (PPI) networks. The approach is supported by both evolutionary arguments and structural evidences, predicting interacting neighbors based on their similarity to the already known neighbors. Intuitively, if two nodes share many of their neighbors then, as opposed to common belief, they might not be connected, but are likely to share some additional neighbors. Thus, instead of relying on indirect connectivity at distances of two steps (d=2) as in the TCP, interactions are predicted based on at least d=3 connectivity, leading to substantially improved predictions, validated both computationally and experimentally. The results can hold more generally, establishing a fundamental principle for link prediction in not only biological systems, but also in social and technological networks, including recommendation systems.

Figure 1:
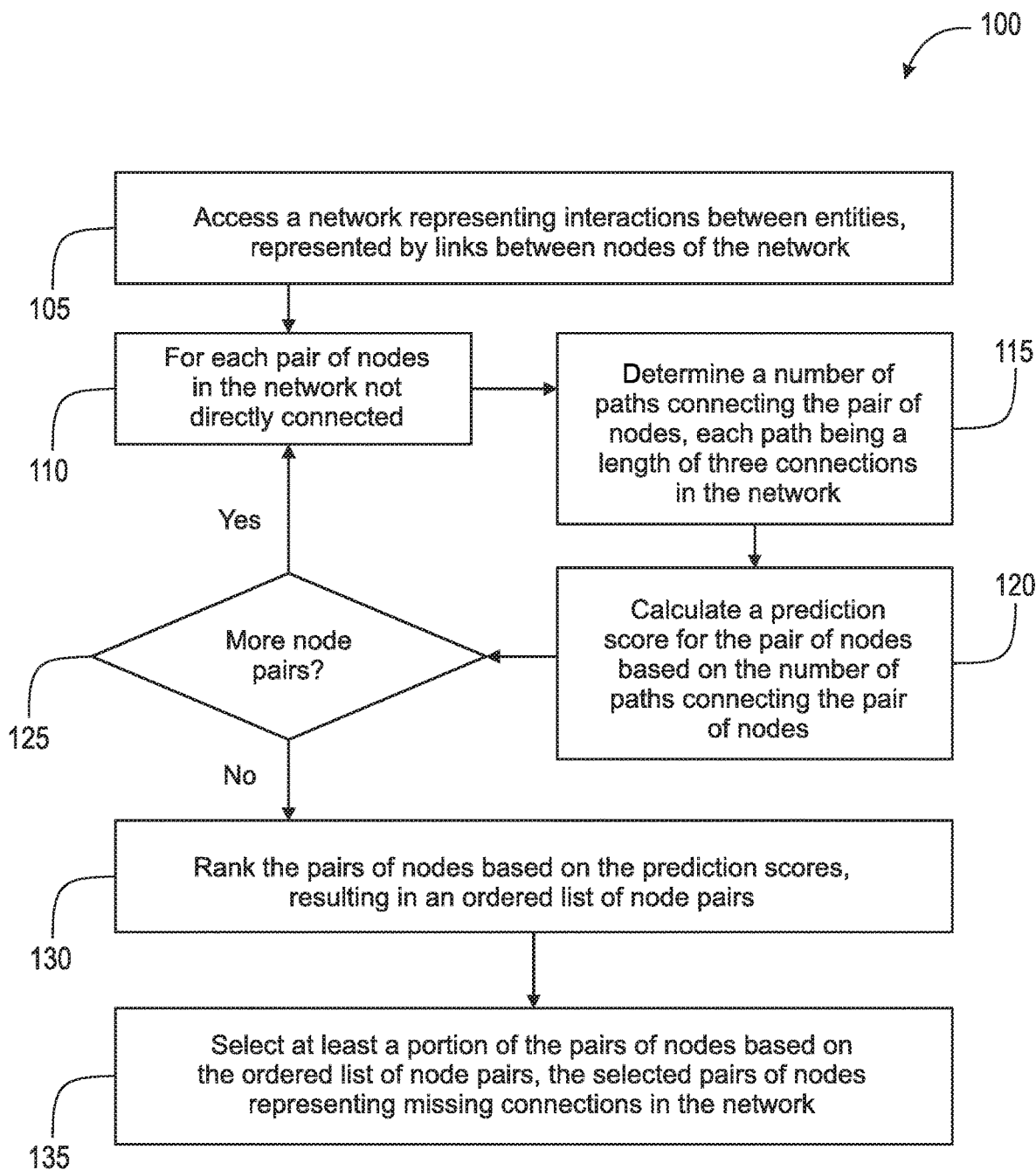
FIG. 1 is a flow diagram illustrating a process of identifying missing connections in a complex network, according to an example embodiment.

FIG. 1 is a flow diagram illustrating an example method 100 of identifying missing connections in a complex network. The example method 100 includes accessing 105 the network, which includes interactions between entities represented by links between nodes of the network. For each pair of nodes in the network not directly connected 110, a number of paths connecting the pair of nodes is determined 115. In one embodiment, each such path has a length of three connections in the network. A prediction score is calculated 120 for each pair of nodes based on the number of paths connecting the pair of nodes. After the prediction scores are calculated for the pairs of nodes not directly connected 125, the pairs of nodes are ranked 130 based on the prediction scores, resulting in an ordered list of node pairs. At least a portion of the pairs of nodes is selected 135 based on the ordered list of node pairs. The resulting selected pairs of nodes represent missing connections in the network.

According to another example embodiment, a complex network can be created by collecting data regarding interactions among a plurality of entities and creating the network from the collected data. Nodes in the network can represent the entities, and connections between nodes in the network can represent interactions between corresponding entities. In a particular embodiment, this can include collecting experimental data about interacting human proteins. There exist about twenty thousand proteins in humans, and about 200 million pairs of such proteins. Collecting the data can be performed with a common assay version in a systematic way, without study biases. A protein interaction network can be created from the experimental data, where the nodes represent either individual protein isoforms or genes, summarizing the information of all related isoforms. The interactions can be represented as undirected unweighted links that can be extended to handle (linear) interaction weights or directional information.

For each protein pair in the network not directly connected, a score can be calculated using, for example, equation (1) described below. This can be accomplished by following and scoring each network path having a length of three and connecting the two nodes. One example score calculation of an individual path can be "1" divided the geometric mean of the degrees (number of interacting partners) of the intermediate nodes, along the path. Alternatively, with only a slight loss of performance (typically 0-20%), the score calculation for a path can be "1", ignoring the degrees. The total probability score for a node pair can be the sum of individual scores for each path. The node pairs can be ranked according to the probability scores, where higher scores correspond to the top ranked predictions.

A probability of existence for each predicted interaction can be estimated in a self-consistent way. For each interacting pair of nodes in the original network, a leave-one-out analysis can be performed, where the interaction is left out of the network and its two end nodes are scored with equation (1) in the remaining network. The leave-one-out score of each original interaction is added to the ranked list of predicted interactions, and the ranked list is used to estimate the probability of existence for each predicted interaction as follows. The probability estimate can be the fraction of original links in a rank window of +/−n predictions around the novel prediction, where n=50 is found in practice to provide reasonable estimates. The estimated probability can be assigned to each predicted interaction, ranked previously using equation (1).

The top predictions for each node in the network can be selected by, for example, using a global or local (for the particular node) threshold, or based on an appropriate probability cut-off. The selected predictions can be published or communicated (e.g., provided to individuals associated with the nodes involved) along with their estimated probabilities. The selected predictions for each node can be integrated to the original network in a weighted manner, where the weight corresponds to the estimated probability of existence for the predicted interaction.

A statistical significance can be assigned to each predicted interaction by comparing the interaction to a pool of randomized networks with the same node degrees. A number of predicted interactions with the highest ranks, significance, or that are selected for some nodes can be subsequently tested experimentally. The sum of estimated probabilities for the selected predictions can serve as an estimate for the overall number of positive hits in the validation experiment. Experimentally validated interactions can be integrated into the network.

The 3-step link prediction (3SLP) platform has the following potential uses:

1. Improve existing recommendation systems, including but not limited to the following examples, such as friendship recommendations (FACEBOOK®) or media content recommendations, for example audio (SPOTIFY®) or video content (YOUTUBE®) recommendations, as well as recommendations for professional positions for job seeking candidates (LINKEDIN®).

2. Identify novel molecular interactions to enable a deeper understanding of molecular function, such as protein-protein, or protein-DNA interactions or drug-target interactions.

3. In annotated networks, such as tagged or labeled networks, the disclosed method can extend the existing annotations to previously unannotated nodes, performing automatic online tagging of media content or functional annotations in biological systems, such as Gene Ontology term or pathway annotations for unannotated proteins.

4. Identify novel disease related genes for complex diseases to help patient stratification and intervention strategies.

5. Identify missing relationships in relational data to improve decision support systems (DSS).

Embodiments can be used with social networks, such as FACEBOOK®, to identify and communicate friendship (or other) recommendations, or with online dating networks, such as OKCUPID®, to identify potential matches. Such embodiments can start with user-reported connection information, representing real-life relationships (e.g., friendships) between real-life people as a network. Profile information can be included in the network by assigning a node to each profile feature and a link connecting it to the relevant profiles. After determining predicted interactions in the network (as described above), the top predicted interactions (relationships) can be communicated to users as friendship (or other) recommendations. If a user confirms a recommendation, the predicted interaction can be added to the network. The embodiments, thus, improve the functionality of social networks.

Embodiments can also be used to identify functional associations, instead of physical connections. In such embodiments, the network can represent functions (e.g., a disease) as additional nodes. The function nodes can be connected to other nodes, representing known associations to the functions. When ranking the predicted interactions, a significance level of each prediction can be assessed by comparing it to randomized instances of the network, and ranking the prediction based on decreasing significance.

Embodiments can be used for functional annotation of proteins (e.g., disease, pathway, or Gene Ontology annotations). Starting with experimentally-validated functional information for a selected set of proteins, predicted interactions in the network can be determining as described above. The resulting predicted connections represent new functional associations for real-life proteins, which can be tested experimentally, thus improving the field of protein interactions.

Embodiments can also be used with professional networks, such as LINKEDIN®, to identify job (or other) recommendations. Such embodiments can start with user-reported job information representing real-life employment between real-life people and companies. Profile information can be included in the network by assigning a node to each profile feature and a link connecting it to the relevant profiles. After determining predicted interactions in the network (as described above), they can be filtered for predicted interactions between users and companies. The top predicted interactions (e.g., job recommendations) can be communicated to users (individuals and/or companies). The embodiments, thus, improve the functionality of professional networks.

With professional networks, such as LINKEDIN®, it is possible to endorse other users with various skills. The embodiments disclosed herein can be used to predict these skills based on available connection, profile, and skill information, in an automatic manner without user intervention. In such embodiments, the skills can be integrated into the network and the predictions can be filtered for user-skill predictions. Top predictions can be communicated to users, who can confirm the recommendations by accepting them. The confirmed recommendations can be added to the network.

Embodiments can also be used for personalized advertising or purchase recommendations. Purchasable items, such as real-life products from AMAZON® or media content (movies or music), can be represented in a network in place of functions (described above). After determining predicted interactions in the network (as described above), the predicted interactions can be communicated to potential buyers in the form of recommended purchases. If a potential buyer purchases the product(s), the corresponding predicted interaction(s) can be added to the network.

Embodiments can also be used for personalized edgotyping using a protein-protein interaction (PPI) network. The predicted interactions provide better coverage and statistical power when used to map network perturbations of disease related mutations for individuals. Embodiments can also be used for personalized medicine, or personalized drug efficacy. Based on individually perturbed PPI networks, it is possible to stratify patients into disease subcategories and predict individual drug efficacy. A protein sequence can be obtained from a patient and applied to the network to determine a disease afflicting the patient, a drug to use for treating the patient, or a potential reaction by the patient to a drug. Such embodiments can be used as a diagnostic test prerequisite for being prescribed a drug.

Example features of 3SLP can include (1) in strong contrast to existing technologies based on the triangle closure principle, 3SLP goes one step beyond d=2 step connectivity and builds upon d=3 step connectivity, identifying the candidate interacting partners from a largely different and much larger pool, (2) a novel way to predict interacting neighbors for a studied node based on their similarity to the already known neighbors, instead of similarity to the studied node itself, (3) suitability to work with network datasets, where some or all the nodes are interacting based on heterophily and not on homophily as traditionally assumed in the field, and (4) besides providing a prioritized list of candidate interactions, 3SLP is able to estimate the probability of existence for each predicted interaction, using a Bayesian calibration based on a leave-one-out cross-validation scheme.

Prior link prediction methodologies rely on the triangle closure principle (TCP), which is proven to be completely wrong for most proteins. Even in the cases when the TCP works, 3SLP provides superior results as indicated by both computational and experimental validations. Example features of 3SLP include (1) ability to identify candidate interacting partners from an order of magnitude larger search pool compared to earlier methods relying on TCP, providing not only higher quality but also more candidates, (2) for protein-protein interaction networks 3SLP performs 2-10 times better than existing methodologies, (3) 3SLP can time and cost efficiently replace additional high-throughput network mapping screens; namely, after the result of the first (incomplete) screen the novel predicted links can be pairwise tested based on this screen instead of performing the same large-scale screen multiple times, recovering predominantly previously observed interaction only, and (4) 3SLP has been validated computationally on a wide range of additional complex networks (for example on social and technological datasets) and found an improved performance in all studied cases, when self-interacting nodes were assumed, indicating that 3SLP is a fundamental and more generally applicable tool than existing methodologies.

Example commercial applications of 3SLP can include (1) improvement of high-throughput network mapping methodologies by replacing additional screens with computational predictions, (2) application to recommendation systems to predict potential interactions between users or products and users, such as personal relationships or media content, (3) identification of novel drug targets, (4) finding of novel disease related genes, and (5) identification of missing relationships for decision support systems.

The following is a detailed example of 3-step link prediction (3SLP) methods and systems.

Biological function emerges from the complex interplay between molecules in cells. While protein-protein interaction (PPI) networks are probably the most studied instances of molecular interactions, current maps are still missing the majority of them. Network based link prediction has a long history in social networks, providing a large arsenal of graph-based algorithms, routinely applied for biological networks as well. Most of these tools are either explicitly or implicitly based on the triadic closure principle, stating that similar nodes (sharing many of their neighbors) are likely to be connected. This principle has only a limited applicability, mostly around proteins forming homomers while it fails for the rest of the interactome. Supported by both evolutionary arguments and structural evidences, disclosed herein is a new way to predict interacting neighbors, namely based on their similarity to the already known neighbors. Intuitively, if two nodes share many of their neighbors then, as opposed to common belief, they might not be connected, but are likely to share some additional neighbors. Thus, instead of relying on indirect connectivity at d=2 steps, interactions can be predicted based on d=3 connectivity, leading to substantially improved predictions, validated both computationally and experimentally. Results are expected to hold more generally, establishing a fundamental principle for link prediction in biological systems, helping to better understand the emergence of biological function and diseases.

Link prediction, aiming to identify missing links in a network using a wide range of information, from sequences to the 3D structure of analogous proteins, is a long-standing problem in the journey to map out the full interactome. Indeed, despite spectacular advances in the experimental mapping of the human interactome, the estimated size of the human protein-protein interaction (PPI) network of $10^5$-$10^6$ interactions, is far beyond the number of experimentally documented interactions so far. The gap is driven by inherent experimental limitations, such as saturation effects and systematic biases, which make it increasingly difficult to map the missing interactions. To obtain a more complete map in a reasonable time-scale, ongoing experimental mapping efforts must be guided by computational predictions, allowing them to focus and prioritize in-depth screening.

With the increasing coverage of the interactome, particular attention has been placed on network-based link prediction, which exploits the patterns of the already mapped part of the interactome to predict missing interactions. Virtually all network-based link prediction methods rely on the triadic closure principle, the expectation that the more common neighbors two nodes have, the more likely that they have a direct link between them (see FIG. 2A). In other words, topologically similar nodes, i.e. those that share many of their neighbors, are expected to establish a direct connection. The hypothesis behind TCP is rooted in social network analysis, originating from archaic times as reflected in "similis simile gaudet" (like rejoices in like), quantifying the observation that the more common friends two individuals have, the higher the chance that they would know each other (see FIGS. 2A and 2B). In the case of protein interactions, the TCP hypothesis states that proteins that share a large number of common neighbors (CN) are likely to participate in the same functional mechanisms, increasing the likelihood that they directly interact with each other. Given its simple interpretation and even simpler implementations, TCP is explicitly or implicitly part of all network-based link prediction mechanisms in the biological space.

Figure 2E:
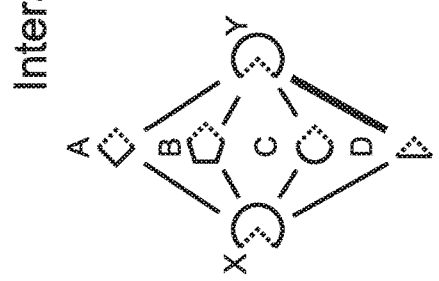
Figure 2D:
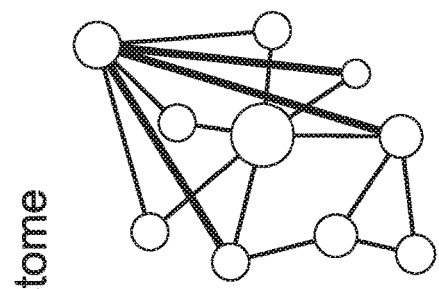
Figure 2D:
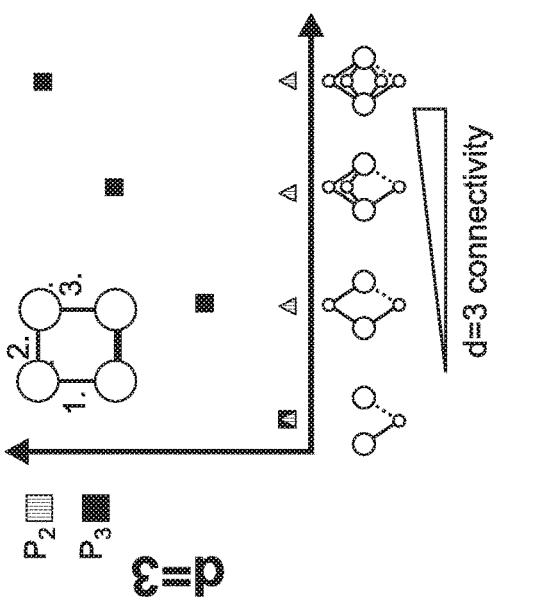
Figure 2F:
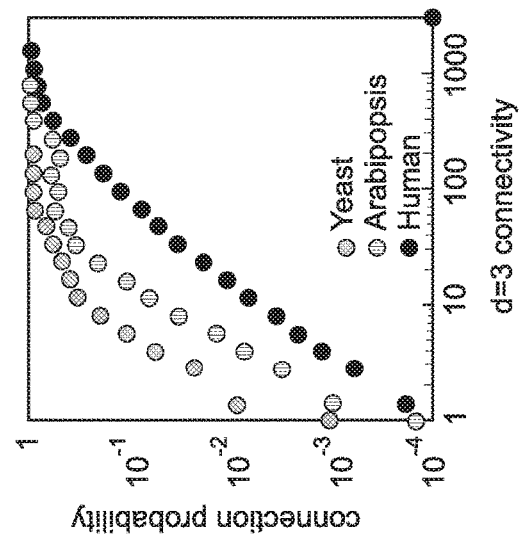

FIGS. 2A-2I are graphs illustrating paths of various lengths and connectivity. FIG. 2A shows the connection probability based on the number of d=2 and d=3 paths as the function of the Jaccard similarity between the two nodes. The triadic closure principle of social networks predicts links based on d=2 connectivity, i.e. by closing possible triangles in the network by connecting the nodes that share the most neighbors. When aiming to find the dotted link, the TCP is the right principle, assuming that the more neighbors two nodes share, the larger the chance that they connect to each other. In this setting, the d=3 connectivity principle is unable to detect the dotted link. FIG. 2B shows TCP predicted links between topologically similar nodes, sharing many of their neighbors. FIG. 2C shows connection probability versus Jaccard similarity in direct systematic interactomes for three species. As opposed to the TCP hypothesis, based on a strong affinity of similar nodes to connect to each other, the opposite tendency is observed, where node similarity prevents direct connectivity, invalidating the TCP for all three studied organisms. FIG. 2D shows the opposite tendency when studying the dotted link between two nodes without any shared neighbors. While this case falls behind the range of TCP, d=3 connectivity can successfully detect such a link, by counting the number of paths at distance d=3 between the two nodes. FIG. 2E shows a representation of the interactome being organized fundamentally differently. Protein-protein interactions are realized by complementary interfaces, where two proteins with similar interfaces (X and Y) might share many of their neighbors while not being able to connect to each other. When looking for missing links in this biological setting, nodes sharing a large number of their neighbors are likely to share some additional neighbors as well, leading to a d=3 connectivity principle. Since natural networks are small worlds, the missing neighbors are relatively far away in the network. FIG. 2F shows a connection probability plotted against d=3 connectivity, finding a positive tendency, indicating a strong connectivity pattern in the studied interactomes at three steps. FIGS. 2G-2I show connection probability in the top 1000 node pairs ranked by different powers of the adjacency matrix, d, representing connectivity at distance d=2, . . . , 8. d=3 connectivity is found to be the most related to direct connectivity in each interactome. Note, that odd distances contain the d=3 paths as special cases.

Checking the validity of the fundamental assumption behind TCP (that the more common neighbors two proteins have, the more likely they will link to each other) can be accomplished by using the Jaccard similarity $J=|N_i \cap N_j|/|N_i \cup N_j|$, where $N_i$ and $N_j$ are the neighbors of nodes i and j, to measure the joined neighborhood of proteins i and j (see Supplemental Information, below, for an alternative similarity measure).

TCP predicts a positive correlation between Jaccard similarity and the probability that two nodes are connected (see FIG. 2A). Interestingly, the opposite trend is observed: the larger the Jaccard similarity, the lower the chance of two proteins directly interacting with each other (see FIG. 2C). This TCP paradox, representing a linking pattern that is the complete opposite of the TCP assumption, is observed in all high-quality direct physical interactomes explored, including human, yeast, and *arabidopsis*.

Shown herein is that the TCP paradox is the result of taking intuitive experience from social networks into the biological space, while ignoring the structural and evolutionary mechanisms that drive protein interactions. Also shown is that by overcoming the TCP paradox, conceptually simple and biologically accurate prediction tools can be designed that not only avoid the pitfalls of TCP, but also significantly outperform all currently-available link prediction tools.

By connecting nodes with common neighbors, TCP relies on network paths of length d=2 (see FIG. 2E). This has, however, some well-known limitations: no method based on TCP can recover a missing link connecting two nodes that lack shared neighbors (see FIG. 2D). As disclosed herein, however, one can go beyond this d=2 connectivity by considering longer paths.

For example d=3 connectivity (see FIGS. 2D and 2E) considers the likelihood that node pairs linked by paths of length d=3 are connected. This d=3 connectivity overcomes the most elementary limitation of TCP, that it cannot predict links for nodes that lack shared neighbors (see FIG. 2B). The more paths of length d=3 that exist between a node pair, the higher the chance that they will also have a direct link between them. In other words, the number of paths of length d=3 correlates positively with the likelihood of two nodes being connected (see FIG. 2F). For completeness, the probability that two proteins, linked by paths of length d=2, . . . , 8 are connected in three organisms was measured, finding that in each the d=3 offers the highest probabilities of being directly connected (see FIGS. 2G-2I). Equally important, the d=3 connection probability is two to three times higher than the d=2 (TCP) connection probability.

To better understand the roots of the TCP paradox and the unusual predicting power of d=3 connectivity, all homomers in the network were identified, capturing all proteins with self-interactions, and heteromers, i.e. the rest of the proteins. Currently, about 12% of the proteins in the human interactome are known to be homomers, hence only about 1% of the protein pairs consist of two homomers. Consequently, the vast majority of protein pairs (87%) in the human interactome capture interactions between two heteromers, representing proteins unable to interact with an identical copy of themselves.

Figure 3A:
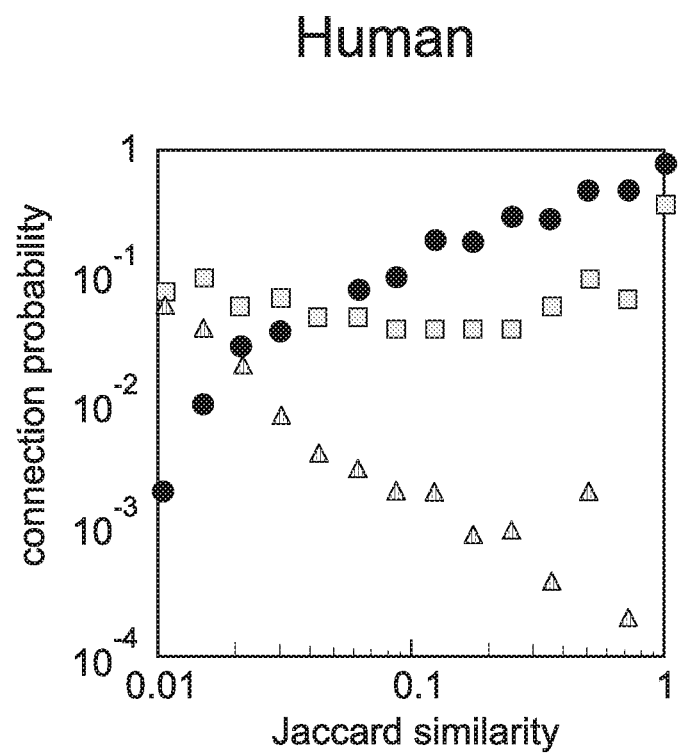
FIGS. 3A-3F are graphs illustrating homomers versus heteromers.
Figure 3D:
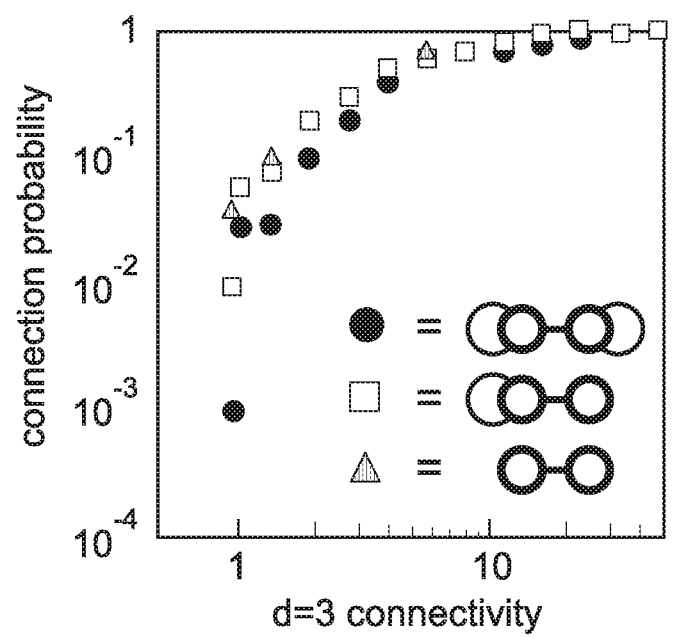
Figure 3B:
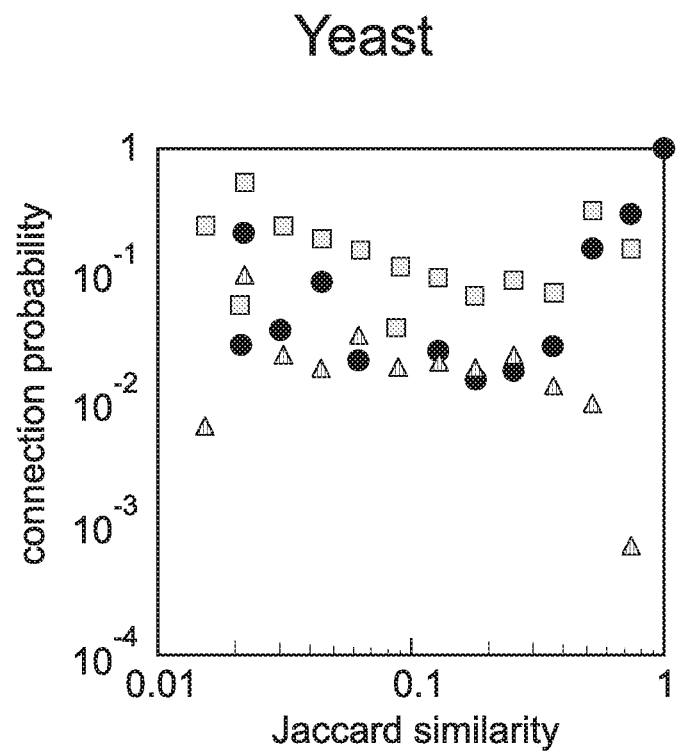
Figure 3E:
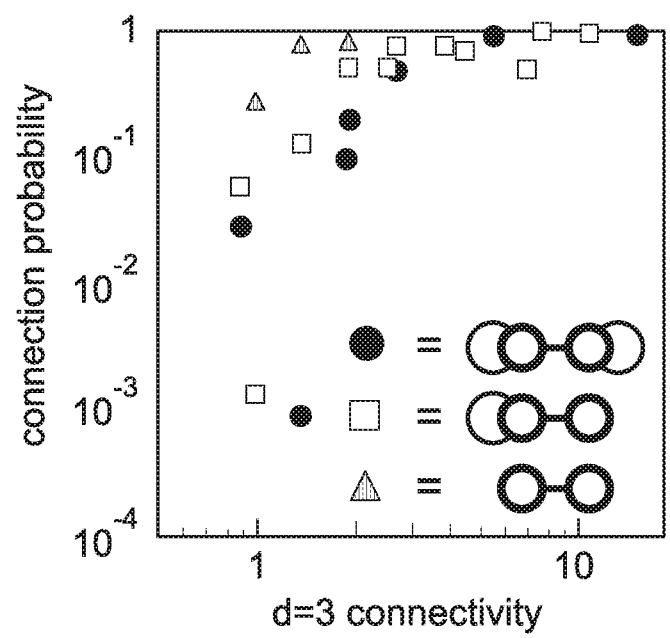
Figure 3C:
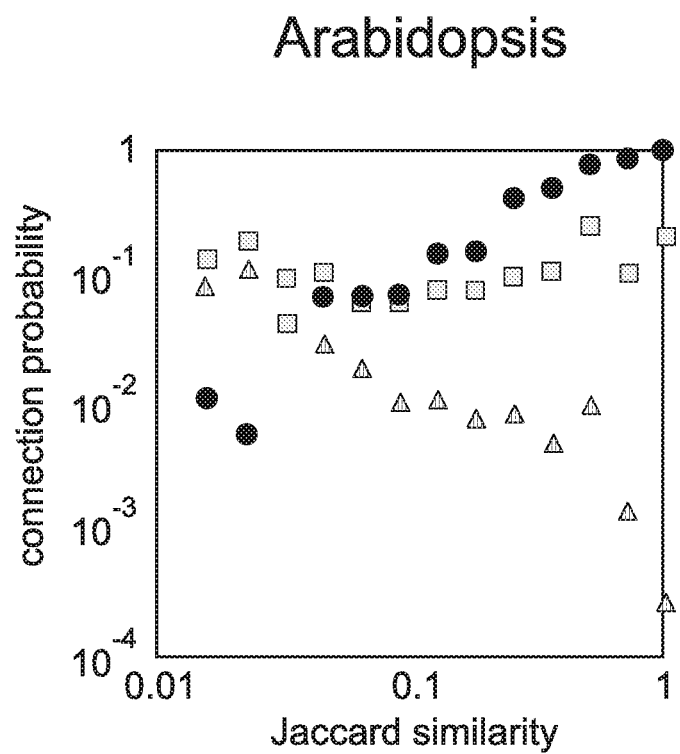
Figure 3F:
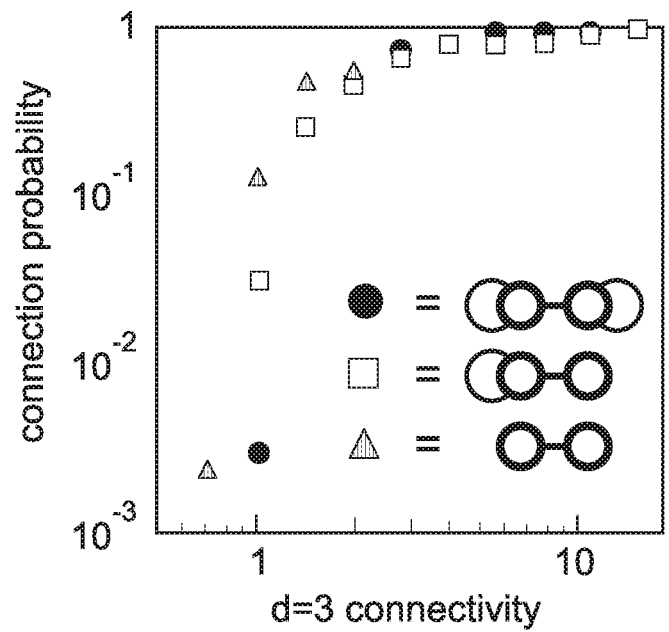

FIGS. 3A-3F are graphs illustrating homomers versus heteromers. FIGS. 3A-3C show connection probability versus Jaccard similarity in the three node pair classes, for the three example interactomes. There is a positive tendency between node similarity and connectivity between two homomers (top, circles) for several orders of magnitudes. While there is no strong tendency between heteromer and homomer nodes (squares), a negative tendency is observed for the vast majority of the node pairs of two heteromer nodes (triangles). Two similar nodes (with Jaccard similarity ~1) are more than a thousand times more likely to be connected if both of them are homomers than none of them. Consequently, the applicability of the TCP is expected to be restricted to the relatively small fraction of homomer node pairs. The data is logarithmically binned based on the Jaccard similarity values. FIGS. 3D-3F show connection probability versus d=3 connectivity in the three node pair classes, for three species. In strong contrast to Jaccard similarity shown in FIGS. 3A-3C, d=3 connectivity expresses an almost identical, strong positive tendency with the connection probability between all proteins, promising a unified way of predicting missing links even without making any distinction between homomers or heteromers.

Interestingly, TCP is valid for homomer pairs: the higher the Jaccard similarity between two homomers, the more likely that there is a direct link between them (see FIGS. 3A-3C). Heteromer pairs follow the opposite pattern: high Jaccard similarity prevents the existence of a direct connection between them. For example, two proteins with a Jaccard similarity close to 1 are more than a thousand times more likely to directly interact with each other if both proteins are homomers than if they are both heteromers (see FIGS. 3A-3C). In conclusion, TCP is valid for homomer pairs, but fails for heteromer pairs. As the number of heteromer pairs vastly dominates over the homomer pairs (87% vs. 1% of the pairs), when this distinction is not made, the dominance of heteromer pairs naturally leads to an overall negative correlation (see FIG. 2C).

The differences between homomer and heteromer pairs vanish when focusing on d=3 connectivity, counting the number of paths of length three between two nodes. Indeed, FIGS. 3D-3F shows the probability that two nodes are connected in the three node pair classes against d=3 connectivity, showing a clear positive correlation. In contrast to FIGS. 3A-3C, where there is qualitatively different behavior for homomers and heteromers, here the data points fall roughly on the same curve for all protein pairs. This indicates that the d=3 connectivity principle accurately captures not only the connectivity patterns of heteromers, but the connectivity pattern of the entire interactome. Two mechanisms can explain the observed patterns.

Figure 4A:
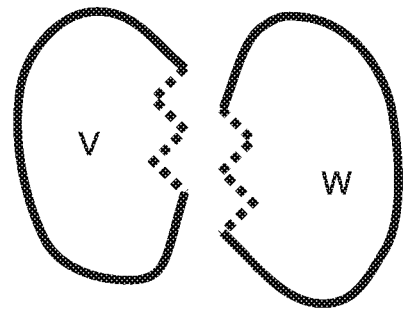
FIGS. 4A-4C are schematic diagrams illustrating examples of protein binding.
Figure 4B:
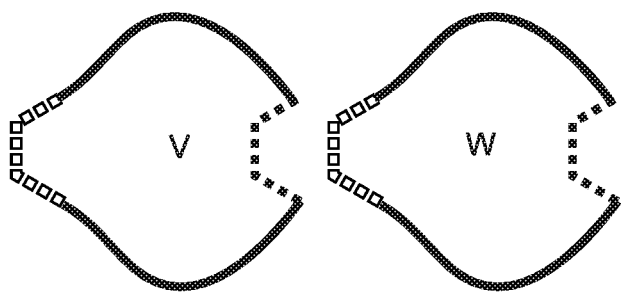
Figure 4C:
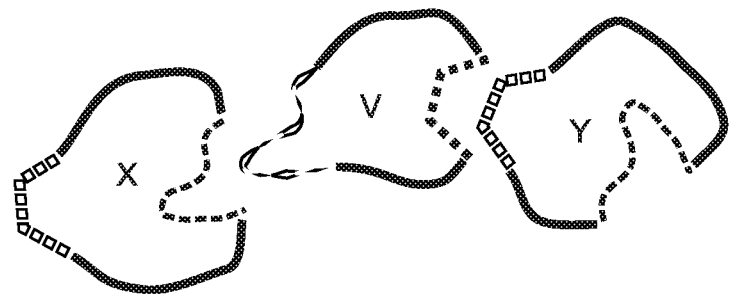
Figure 4D:
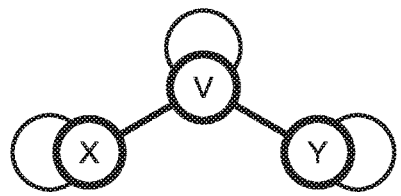
FIGS. 4D-4K are graphs illustrating examples of protein connectivity.
Figure 4H:
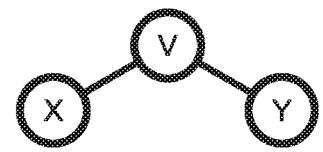
Figure 4E:
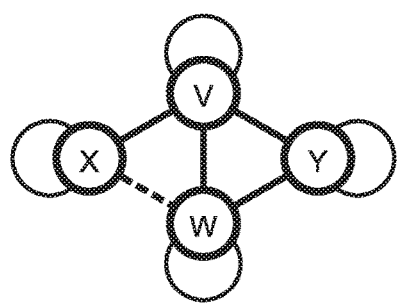
Figure 4I:
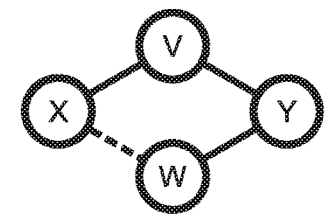
Figure 4F:
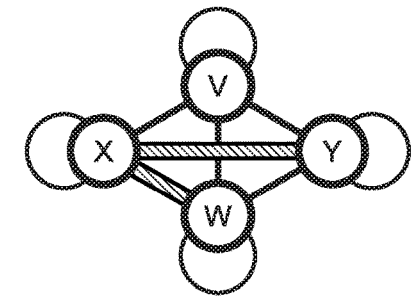
Figure 4J:
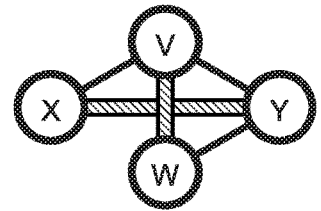
Figure 4G:
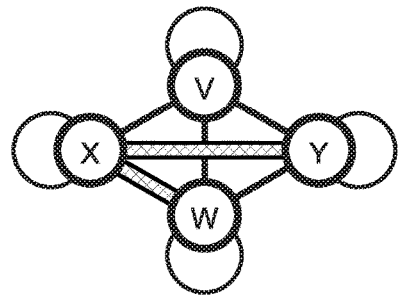
Figure 4K:
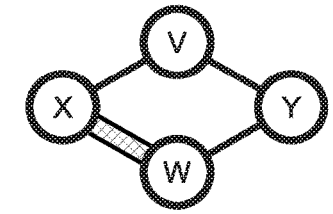

FIGS. 4A-4C are schematic diagrams illustrating protein binding, and FIGS. 4D-4K are graphs illustrating protein connectivity. FIGS. 4A-4C illustrate the structural reasons of the observed connectivity patterns, different binding interfaces being illustrated by different colors on the proteins. In order to form a self-interaction, homomer proteins require either a self-interacting interface (FIG. 4A) or two complementary interfaces (FIG. 4B). Heteromer proteins with similar interfaces are typically not connected, while share many of their neighbors. FIGS. 4D and 4H illustrate that, starting from an original protein (V), gene duplication leads to fundamentally different network structures. FIGS. 4E and 4I illustrate that homomers typically lead to locally dense cliques, while heteromers lead to much sparser, locally bipartite structures. Finding a missing (dotted) link appears to be a very different problem in the two cases. FIGS. 4F-4K illustrate that in a dense graph of homomers, both the d=2 (TCP) and d=3 principles are able to detect the missing link. However, TCP fails to correctly identify the missing link between two heteromers, while the d=3 connectivity principle (FIG. 4G) is expected to succeed in all classes.

As protein interactions primarily require complementary interfaces, a homomer protein must already possess both complementary interfaces (FIG. 4A), or an interface that is able to bind to itself (FIG. 4B). Consequently, if two homomer proteins interact, they are likely to share their neighbors as well, connecting to the same interface or interfaces that establish the self-interaction. Moreover, the more neighbors that two homomers share, the more likely that they interact, similarly to social networks.

In contrast, the interaction partners of a heteromer protein must have complementary interfaces (see FIG. 4C). Two heteromers X and Y that have the same interface will have common neighbors (for example V), as they will interact with all proteins that have complementary interfaces. Since X and Y are heteromers, the shared interface is unable to connect to itself, hence X and Y will probably not directly interact. On the other hand, if two heteromer proteins interact (e.g., X and V) then they could only share common interaction partners, that have both complementary interfaces, which is again unlikely. To conclude, the structure based reasoning predicts that two proteins that share multiple neighbors (X and Y in FIG. 2D) are likely to share some additional neighbors (e.g., D), as indicated by the blue links. This is the essence of the d=3 connectivity principle, connecting a neighbor (D) of protein X to protein Y in FIG. 2D, in three steps on the graph.

A similar conclusion is reached looking at gene duplication, a key evolutionary mechanism responsible for the emergence of new proteins. If protein V duplicates, the duplicated node (W) will maintain the links of the original protein (see FIGS. 4E and 4I). As homomer proteins can interact with themselves, the new protein (W) will have a direct link to the original protein (V) as well (see FIG. 4E). In contrast, a duplicate of a heteromer protein will interact with the neighbors of the original heteromer, but will lack a direct link to it (FIG. 4I). Starting from an original interaction between a pair of proteins, gene multiplication leads to fundamentally different network patterns, ranging from a fully connected clique to bipartite graphs. While mutations and diversification perturb these connectivity patterns, the overall topological differences in the neighborhood of homomer and heteromer proteins will prevail after duplication.

Next, the predictive power of d=3 connectivity was checked against the predictions of TCP. It was found that, to the contrary of TCP, the d=3 connectivity is able to find a missing link (FIG. 4K), even for heteromers. The reason is that gene duplication induces the pattern that proteins sharing a large number of their neighbors are likely to share with some further neighbors, even if they are not directly connected. Hence, a missing partner is one step further away than expected by TCP, where nodes at distance d=2 would be connected.

Both the structural and evolutionary arguments suggest that similar proteins, i.e. those sharing either an interface or common evolutionary roots, are not necessarily connected, but are likely to connect to the same neighbors. Consequently, a potential interaction partner of a protein is not always similar to this protein, but is likely to be similar to the existing partners of the protein, underlying the d=3 connectivity principle.

Link prediction: Taken together, the d=3 connectivity principle describes the observed connectivity patterns of both heteromer and homomer proteins, in strong contrast to the d=2 connectivity (TCP), which correlates with the direct connectivity between homomer pairs only.

To turn this observation into a predictive framework, d=3 connectivity is quantified in PPI networks, in a way to account for the broad range of observed degrees. In FIGS. 2A-2I and FIGS. 3A-3F, the number of paths at d=3 were measured, equivalent to the third power of the adjacency matrix, $A^3$. Since high degree hubs induce a tremendous number of shortcuts in the network, improved predictions are expected by properly normalizing with the degrees of the intermediate nodes in the paths, similarly to various implementations of TCP.

To reduce the overwhelming effect of the hubs, the degree-normalized adjacency matrix $\tilde{A}=D^{-1/2}AD^{-1/2}$ can be used, where D is the diagonal degree matrix, measuring the d=3 connectivity as $A\tilde{A}A$. In other words, for each pair of nodes i and j, a degree normalized d=3 connectivity score is assigned:

$$s_{ij} = \sum_{m,n} \frac{a_{im}a_{mn}a_{nj}}{\sqrt{k_m k_n}} \qquad (1)$$

where $k_m$ is the degree of node m. The hypothesis is that node pairs with the highest scores are most likely to be connected by missing interactions.

To computationally verify the validity of equation (1), 50% of the links were removed and the recovery rate for the most highly ranked 2000 pairs was measured. The results were compared with the predictions of TCP and those of the preferential attachment (PA) principle, a link prediction method that is not based on the TCP. Indeed, PA assumes that the probability of a link between two nodes is proportional to the product of their degrees. TCP is represented by its simplest implementation, CN, counting the number of common neighbors. It was found that d=3 connectivity outperforms both the TCP and PA on the human interactome, independently of whether the node pairs are homomers or heteromers.

Figure 5A:
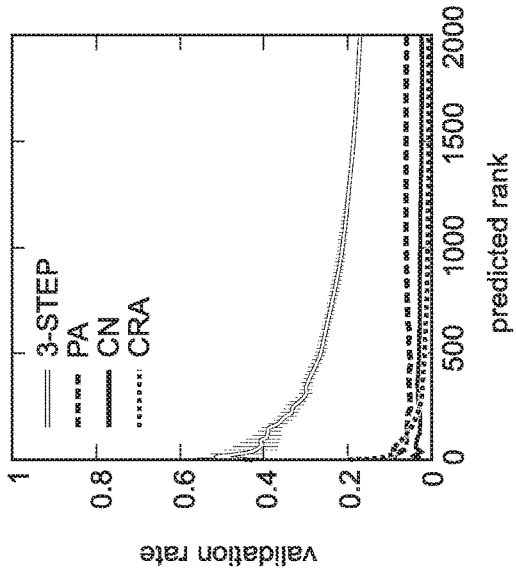
Figure 5B:
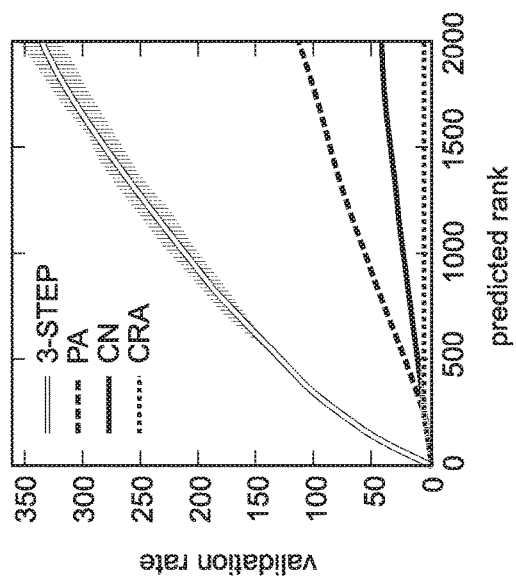
Figure 5C:
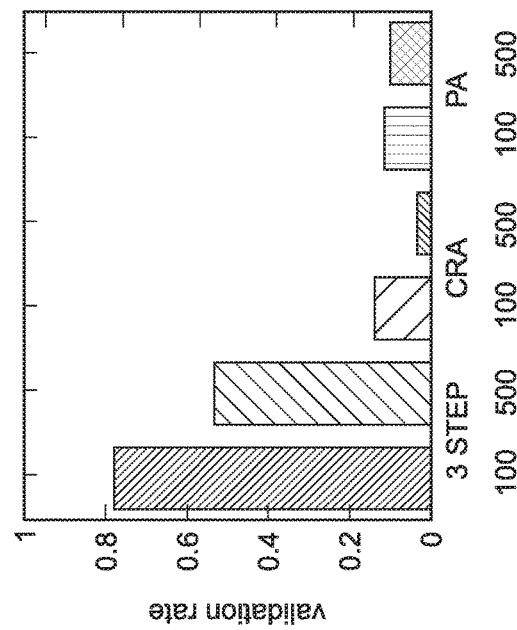
Figure 5D:
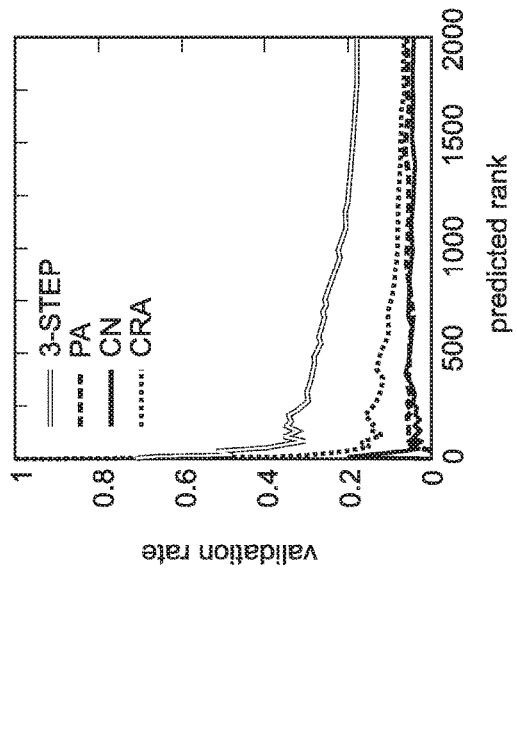
Figure 5E:
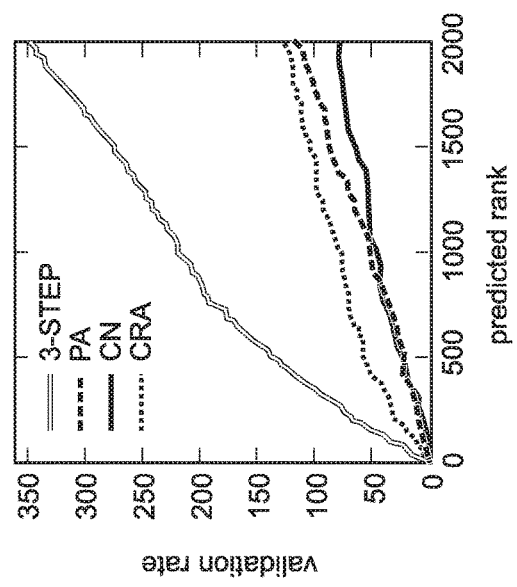
Figure 5F:
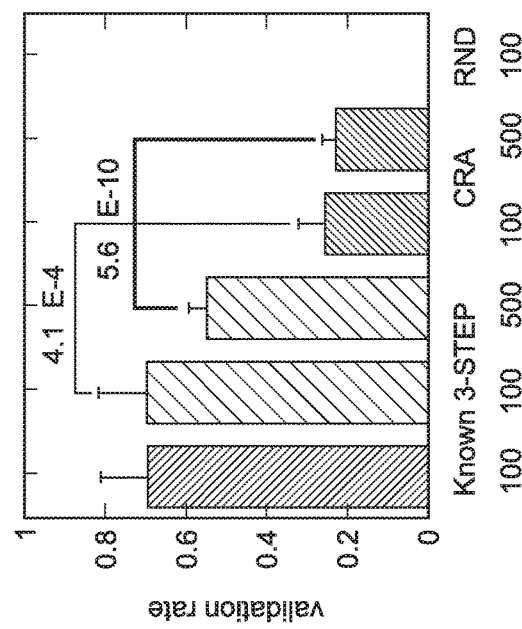
Figure 5J:
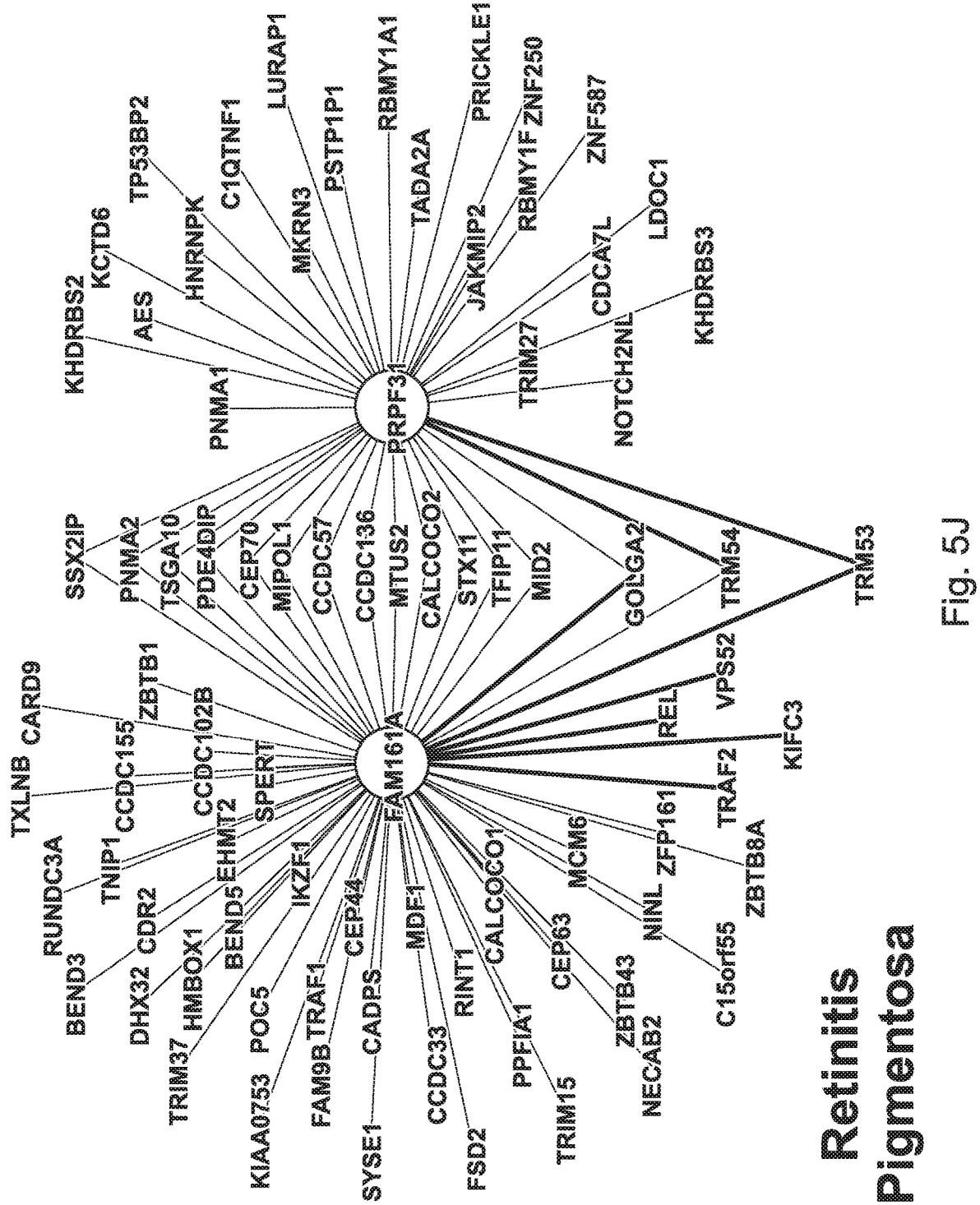
Figure 5K:
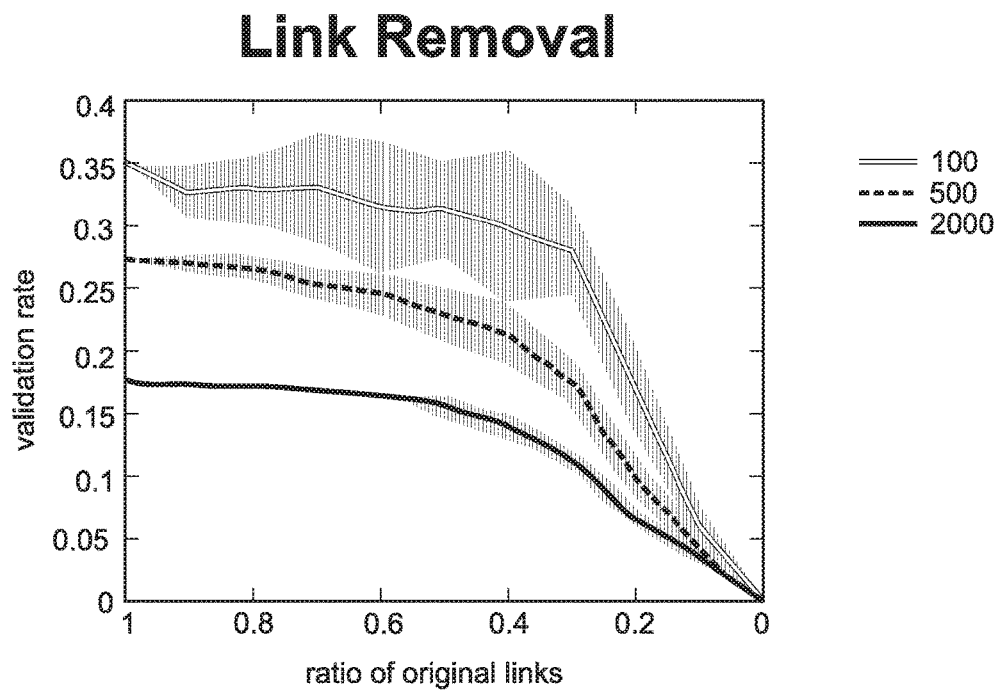
Figure 5L:
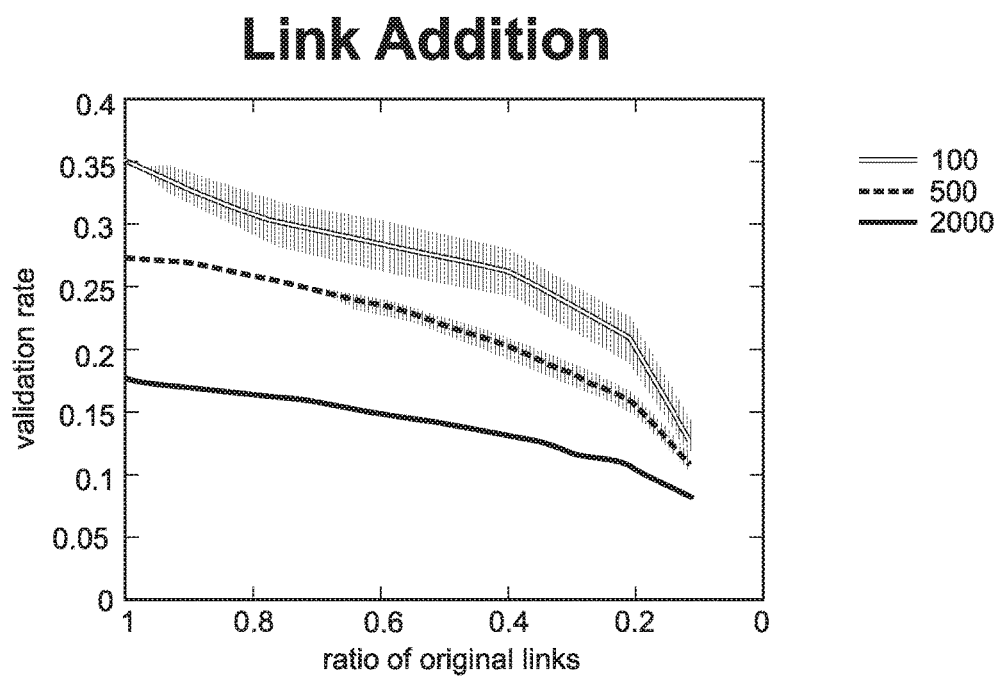

FIGS. 5A-5L are graphs illustrating computational and experimental validation on the human interactome. FIGS. 5A-5C show results of a computational validation on the filtered human interactome, containing no keratins and restricted to one ORF per gene. 50% of the links were chosen randomly as the input for link prediction, averaged over 10 realizations. In all cases, the shaded range indicates the standard deviation of the results over 10 realizations. CRA stands for the community resource allocation index, performing best in the high-throughput validations (FIGS. 5D to 5F). FIG. 5C shows the validation rate as a histogram for the top 100 and 500 predictions, respectively. FIGS. 5D-5F show high-throughput experimental validation. The predicted links were tested against the human interactome, HI-III-123, generated with the same experimental assay as the input interactome (for details, see Supplemental Information). Besides the previously shown methods, 23 different methods were tested this way, highlighting CRA as the best available method for the top predictions. For a proper calibration, in F a positive set of 100 known interactions ("Known") and random set ("RND") of 100 node pairs were selected, connected to the same nodes as the top 500 predictions of the d=3 connectivity method. FIGS. 5G-5I show direct validation with pairwise testing of the top 500 predicted links of CRA and the disclosed method. Again, the d=3 connectivity principle (blue) significantly outperformed CRA, providing 2 to 3 times better results. The pairs where the experiments were inconclusive were left out of the analyses. Remarkably, according to both experimental tests, the top 100 predictions validate about as well as the selected set of known interactions. FIG. 5J illustrates experimentally validated predicted links with d=3 connectivity for retinitis pigmentosa (RP). The gray links represent all known interactions in HI-filtered for the two RP proteins, FAM161A and PRPF31 (yellow nodes). Eight of the novel, experimentally-validated links (blue) connect to at least one of these RP proteins, enabling a more complete understanding of the RP disease mechanism, including the top predicted link FAM161A-GOLGA2. As a manifestation of the link prediction principle, it is shown that if two nodes (yellow) share many of their neighbors then they might share even more, even if they are not directly connected as would be expected by the TCP. FIGS. 5K and 5L show a robustness analyses of the predictions with high-throughput validation against link removal (FIG. 5K) or additional random links (FIG. 5L) at the to 100, 500 and 2000 predictions, respectively. The method is robust even when less than 50% of the links are kept or are original. The standard deviation of the results is indicated by shaded ranges over the 10 realizations.

In the following, the combined performance of equation (1) is explored, not distinguishing between homomers or heteromers. It was found that for all studied organisms the d=3 connectivity principle significantly outperforms the d=2 connectivity and PA, having several times higher validation rates. Evidence was obtained that that results hold more generally, independently of the organism (fruit fly, mouse, C. Elegans, S. Pombe) and network origin (literature derived, Lit-BM-13, Biogrid), structure-based (Interactome3D) or mass-spectrometry based co-complex membership datasets (Bioplex, Qubic).

Experimental validation: To experimentally test the predictive power of equation (1), the study was restricted to a filtered human interactome (HI-filtered) of N=3727 proteins and E=9433 interactions between them, containing only one open reading frame (ORF) per gene and no keratins (see Supplemental Information) for HI-II-14. For a high-throughput validation, it is ideally needed to repeat the entire experimental screening independently, for the same proteins under identical experimental conditions. Such a dataset, consisting of three independent screens, has been recently generated (HI-III-123, REF). Note, that as any individual dataset, HI-III-123 is still incomplete, containing only 42.4% of the interactions in HI-filtered. Still, HI-III-123 allows a systematic evaluation of all computational methods, in the full range of predicted scores. It was, again, found that equation (1) significantly outperforms the other methods. For comparison, 23 link prediction methods were tested, finding that there is one method, called community resource allocation index (CRA) that performs best for the top predictions. CRA relies on a strong connectivity at both d=2 and d=3, hence its predictions represent a subset of the predictions disclosed herein. To control the performance of the experiment, a selection of known links in the interactome ("Known") and random protein pairs ("RND") were used as benchmarks (for details, see Supplemental Information). The obtained validation rate of the top 100 predictions, about 35%, is indistinguishable from the validation rate of the selected set of known links (35%) (see FIG. 5F), indicating that the top predictions are as reliable in reproducibility as the already known protein-protein interactions. In the random set (RND) no validated hits were found, even though ~1-5% would still indicate a high quality experiment.

To obtain a more complete validation that is not limited by the incompleteness of the existing interactome maps, direct pairwise testing experiments for the top 500 predicted links were also performed (FIG. 5G-5I). It was found again that the top predicted links validate with the same rate as the already known interactions (FIG. 5I). In particular, d=3 connectivity performs about three times better at the top 500 predictions than CRA, the best performing method in the literature.

Given the unavoidable presence of false negative and false positive interactions in the datasets, it was tested whether the results are robust against data incompleteness and noise. For this, a fraction of the links were randomly removed. In the high-throughput setting, it was found that the validation rate of the predicted interactions was fairly stable up to removal of even 60-70% of the interactome (see FIG. 5K). While the false positive rate in the human interactome is expected to be very low (based on the low RRS discovery rate), it is typically not quantitatively known. To test the robustness of the technique against such a noise factor, a number of random links were included in the network. Again, the validation rates were found to be robust, even when the number of random links exceeds the number of original links (see FIG. 5L).

Case Study on Retinitis Pigmentosa: The ability to predict previously undetected parts of the interactome offers the possibility to gain insights about the mechanism of disease-related mutations. For this, the disclosed link predictions can be selectively tested for known disease genes, while follow-up studies can perform functional assays and edgetyping experiments in order to illuminate the function of these new interactions. To illustrate this potential, one can focus on the top predicted (and experimentally validated) link that connects FAM161A—involved in Retinitis Pigmentosa, (RP)— to GOLGA2 (see FIG. 5J). RP is a genetic disorder leading to the loss of the retina's light sensitivity through progressive degeneration of the photoreceptor cells, being the leading cause of inherited blindness, lacking a cure. Remarkably, FAM161A and GOLGA2 share no neighbors in the HI-filtered interactome, hence a link between them could not be predicted by any TCP based method. In addition to the interaction of FAM161A with GOLGA2, five more novel interacting partners for FAM161A were identified, namely TRAF2, KIFC3, VPS52, REL, and TRIM23. TRIM23 is also identified as a new interacting partner for PRPF31 besides TRIM54. Three of the new interacting proteins (GOLGA2, TRIM23, and VPS52) play an important role in the Golgi apparatus, underlying the role of the Golgi apparatus in RP, as shown recently, where the interaction between FAM161A and KIFC3 has also been identified. As a summary, this case study serves as an example of the intuitive picture in FIG. 2I, where two proteins sharing many of their neighbors are likely to share some further neighbors.

Discussion: Protein-protein interactions (PPI) serve as a rich source of information, especially fruitful in predicting gene function, pathways and complexes, while playing a central role in a mechanistic understanding of cellular function under both normal and disease conditions. Besides providing an essential basis for functional proteomics and drug discovery, there is increasing evidence that disease related mutations are often manifested as perturbations of the physical interactions of the proteins in the human interactome. Moreover, gene mutations related to specific diseases organize into localized neighborhoods in the interactome, indicating the existence of disease modules. These observations establish the foundations of a systematic network framework to better understand human diseases. However, most of the human interactome is still uncharted, hindering further progress, such as a obtaining a detailed mechanistic understanding, e.g. by performing edgetyping analyses of disease mutations. In order to obtain a deeper understanding, the long-standing problem of network link prediction was revisited, and it was found that frequently-used methods are based on incorrect assumptions about the structure of PPI networks.

The computational analyses of biological networks is very challenging, affected heavily by study biases, incompleteness and false positive interactions. Even the most basic visualization of the interactome is prone to failure, known as the "hair ball" problem. Having no better options, the disclosed system-level intuition stems mostly from an understanding of social networks, where node (topological) similarity and connectivity are known to be correlated, according to the TCP. This hypothesis only works for homomer proteins, while fails for most of the proteins in the PPI network. As an alternative link prediction paradigm, a d=3 connectivity principle can be used, supported by both evolutionary and structural arguments. Both TCP and d=3 connectivity is based on the existence of node pairs sharing many of their neighbors. While the TCP intends to connect these two (topologically similar) nodes to each other, in the same situation the d=3 connectivity connects one of the not yet shared neighbors of them to the other node. Intuitively, a candidate neighbor should be (topologically) similar to the known neighbors of the studied protein and not to the protein itself.

After computationally checking the superior performance of d=3 connectivity on three species, the top predictions were validated experimentally for a restricted human interactome, HI-filtered. The top predictions validated with the same rate as already known interactions in both of the high-throughput and pairwise tests, indicating an optimal performance. This performance is found to be highly robust against incompleteness (link removal) or noise (randomly added links), qualifying the disclosed method to be used over a wide range of potential datasets. The disclosed method can be a great help to obtain more complete, high-quality interactomes, enabling a more detailed mechanical understanding of complex diseases. When put in a broader perspective, the results will likely lead to an improved set of biological network analyses methods that rely on more realistic assumptions than those borrowed from social sciences.

Supplemental Information

A. Analyzed Networks

In order to compensate for the incompleteness and strengths and weaknesses of each dataset, the results were tested on several interactomes over seven species. As a starting point its was intended to understand the structure of PPI networks including only direct (binary) physical interactions. For this purpose systematic, binary networks generated with yeast-two-hybrid experiments were used, such as the human (HI-II-14), yeast, and *arabidopsis* interactomes. Even though these networks were obtained in a systematic way to avoid study biases, they have a limited coverage and there might be certain biological limitations, leading to biases e.g. to a depletion in membrane proteins or potential overrepresentation of keratins. For a comparison, literature-curated PPI networks of direct physical interactions were included, such as Lit-BM-13, or the Biogrid datasets. In the case of the Biogrid datasets, only "direct interactions" and proteins assigned to the correct "taxid," specific to the studied species were considered. These networks are prone to study biases, meaning that highly studied protein (with many publications) have a higher degree and a more complete coverage.

To show that the results hold more generally, beyond binary physical interactions, also considered were cocomplex proteomics datasets, such as the Bioplex and QUBIC networks, listing protein-protein associations (PPAs). Besides incompleteness, another issue is the (mostly unknown) number of false positives in these datasets. To test the results more precisely, also included was the Interactome3D network to see if the results hold also for the high quality but sparse set of available interactions with structural evidence.

B. Evaluation with Various Quality Measures AUC is Calculated as:

$$AUC = \frac{n' + 0.5n''}{n} \quad (2)$$

where by randomly selecting n pairs of a positive and negative link, larger score n' times and an equal score n" times is obtained for the positive link. The AUC value is between 0.5 and 1 and a higher value is assumed to indicate a better performance.

The Precision is defined as:

$$P = \frac{L_p}{L} \quad (3)$$

where $L_p$ is the number of positive links in the top L number of predictions. The precision is between 0 and 1 and higher precision value means higher accuracy.

Being a frequently used performance measure for web search companies, the Normalized Discounted Cumulative Gain (NDCG) is known to be able to select the better ranking between any two, substantially different rankings. For binary classification the NDCG is given by:

$$NDCG = \frac{\sum_{i \in P} \frac{1}{\log_2(i+1)}}{\sum_{i=1}^{|P|} \frac{1}{\log_2(i+1)}} \quad (4)$$

where the summation in the nominator runs over all positive instances, while the summation in the denominator quantifies the deal case, where the positive instances are the top ranked predictions. In practice, to deal with extreme degeneracies, for the candidates with a zero score, the last possible rank was assigned to each of them.

C. Calibration of the Predicted Score

A leave one out approach was used to assign predicted scores to the existing links. By having at hand all the scores for the existing and predicted links, a naive bayesian approach was used to estimate the probability that a predicted links is real. To be precise, the probability of a link to exist in a window of (at most) w=50 existing links was calculated before and after a link in the ranked list.

D. Details of the Pairwise Testing Experiment

In the experiments the top 500 predictions of the d=3 connectivity principle was tested against the top 500 predictions of CRA on the human network, HI-filtered. Additionally, for a proper benchmarking, included were literature curated, interactions with multiple evidence (Lit-BM-13), as well as a set of positive reference interactions (PRS) and 100 known interactions connected to at least one of the nodes in the top 500 predictions (Known). On the other side, to control the false positive rate, a set of random node pairs in the random reference set (RRS) and a similar set off 100 pairs centered around the top 500 predictions (RND) were selected. Summarizing all these pairs results in XXX non-redundant pairs.

In the experiments, each pair has been tested in both Y2H orientations (AD-DB vs. DB-AD) and a pair is considered to be validated if it was found in at least with one of the orientations. In the Y2H screening fresh overnight cultures of individual Y8930:DB-ORF yeast strains were mated against Y8800:AD-ORF strains. The growth phenotype of all pairs was tested in individual pair-wise tests. Previously developed liquid mating strategy was used with direct spotting of diploid yeast cells in 100 ul of YEPD using liquid handling robotics. After overnight incubation at 30° C., 2 ul of mated yeast culture were transferred to 100 ul of SC-Leu-Trp media to enrich for diploids. After overnight growth at 30° C., a 5 ul aliquot of the liquid culture was robotically spotted, onto both SC-Leu-Trp-His+3AT and SC-Leu-His+3AT+CHX solid media. After an incubation of three days, diploids that gave rise to growth on SC-Leu-Trp-His+3AT and failed to grow on SC-Leu-His+3AT+CHX were classified as pairwise positives. To confirm identity of the pairwise positive interactors, colonies were picked and processed for sequencing using the X×X system and aligned to the corresponding ORFs. Open-reading frame (ORF) clones encoding human proteins were obtained by PCR-based Gateway recombinational cloning following a protocol previously described. Prior to Y2H screening, diploid DB-ORF yeast strains were tested for auto-activation of the GAL1::HIS3 reporter gene in the absence of any AD-ORF plasmid as described. Individual DB-ORF yeast strains were mated with the Y8800 yeast strain transformed with empty pDEST-AD-CYH2 vector. Diploid cells were first selected on solid SC-Leu-Trp media and then transferred onto solid SC media lacking leucine, tryptophan and histidine and containing 1 mM 3AT (SC-Leu-Trp-His+3AT). Any DB-ORF yeast strains that grew on SC-Leu-Trp-His+3AT solid media were considered auto-activators and removed from the collection of DB-ORF yeast strains to be screened.

In principle, the nodes of the top predictions might have special characteristics which locally modify the recovery rate of their links. To be more specific, the selected positive set ("Known" links) contains 100 randomly selected known links (in HI-filtered) around the nodes involved in the top 500 predictions. Selecting a negative benchmark set is much more problematic due to the high false negative rate of the current experimental techniques. A frequently used alternative is the use of a random set, where node pairs are selected randomly and expected to be recovered with a rate given by the density of the network which is predicted to be less than 1% for the complete interactome (currently ~0.14% in HI-filtered). Similarly to the positive set, 100 random links ("RND") were selected in a way that at least one of the nodes is involved in the top 500 predictions. Note, that for a fraction of pairs the experiments turned out to be inconclusive, eventually left out from the analyses. Each pairwise tested positive pair was sequence confirmed by Sanger Sequencing with GeneWiz.

E. Functional Validation Based on GO-Term Analyses

While gene ontology (GO) terms are frequently used to evaluate the functional relevance of predicted interactions, proteins that are not connected but have a high degree of similarity might be more similar in their GO-annotations than interacting proteins. Indeed, the observations question the legitimacy of using GO-terms or functional annotations to evaluate the quality of the predicted physical links.

The annotations are obtained from the Gene Ontology Consortium (http://www.ebi.ac.uk/GOA). In order to avoid noise and circularity, the analyses were restricted to proteins only mapped to Entrez gene IDs, excluding the "NOT" qualifiers and considering only high confidence annotations associated with the evidence codes EXP, IDA, IMP, IGI, IEP, ISS, as listed below.

Experimental:
Inferred from Experiment (EXP)
Inferred from Direct Assay (IDA)
Inferred from Mutant Phenotype (IMP)
Inferred from Genetic Interaction (IGI)
Inferred from Expression Pattern (IEP)
Computational:
Inferred from Sequence or structural Similarity (ISS)

Note, that there were no instances of ISO, ISA or ISM annotations. The input dataset was generated on 2016-11-28 09:32. The following version was used: http://purl.obolibrary.org/obo/go/releases/2016-11-26/go.owl goa_human.gaf.

F. Topological Similarity Vs. Connection Probability

There are several established ways to quantify topological similarity, most of them differing only in the (degree) normalization scheme of the number of shared neighbors, frequently used for similarity-based link prediction in favor of the TCP. To further support the findings shown in FIGS. 2J-2I, shown in FIGS. 6A-6D is the same dataset when the similarity is quantified by the hypergeometric p-value. The results suggest, that in datasets focusing on complexes or homomer dominated regions of the interactome, the TCP might provide reasonably good predictions, however, on systematic interactomes, dominated by heteromers, there is a need to go beyond the TCP and, as indicated before, the natural candidate is to use a d=3 connectivity principle. The universality of this observation is reflected in the fact that it replicates for all studied networks, as shown in FIGS. 7A-7G with the Jaccard-index as a similarity measure.

Figure 6A:
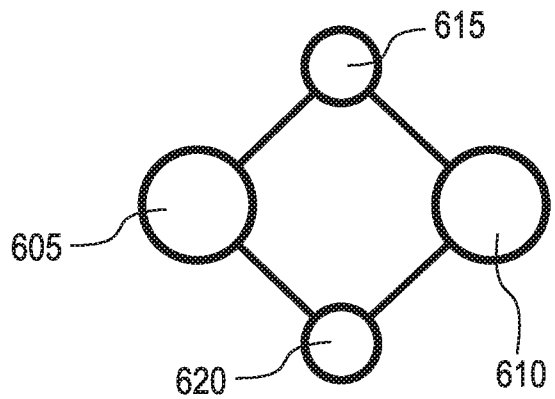
FIGS. 6A-6D are graphs illustrating a simplified example of biological link prediction.
Figure 6B:
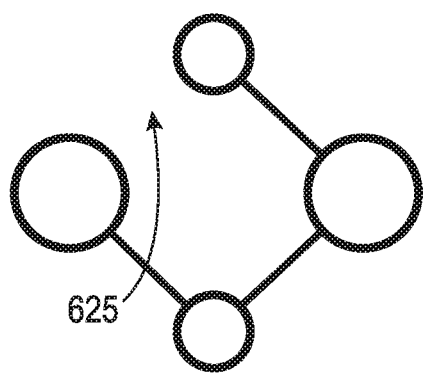
Figure 6C:
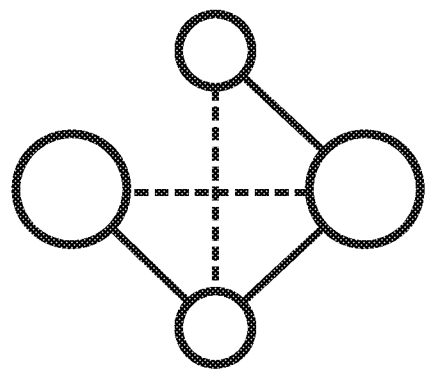
Figure 6D:
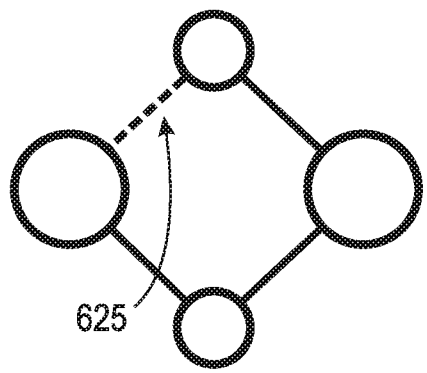

FIGS. 6A-6D are graphs illustrating a simplification of biological link prediction. FIG. 6A represents that redundancy is a key element of biological networks. Typically there are alternative pathways, meaning that two (functionally similar) nodes (e.g., nodes 605 and 610) are connected through multiple shared neighbors (e.g., nodes 615 and 620). FIG. 6B represents that current maps of the network are incomplete, missing many links (e.g., missing link 625). FIG. 6C represents the celebrated triadic closure principle that predicts links based on closing possible triangles in the network, while often missing the true opportunities. FIG. 6D represents a missing link 625 in a redundant network that can be conveniently uncovered by the d=3 connectivity principle, by closing paths of length 3.

Figure 7A:
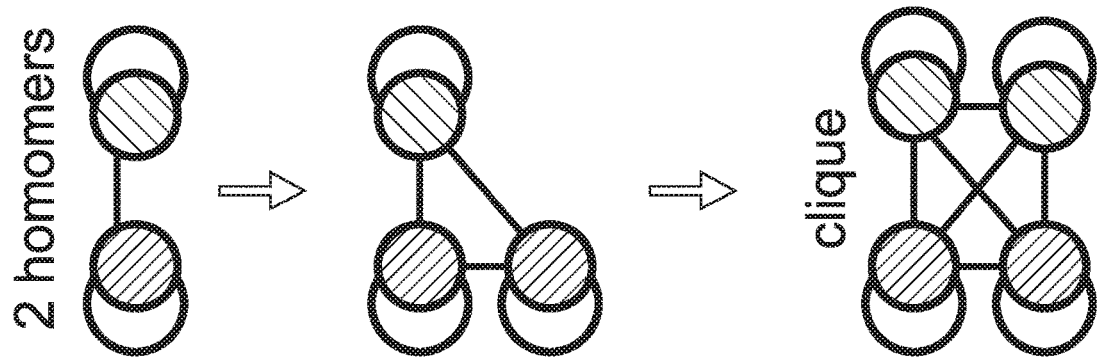
Figure 7B:
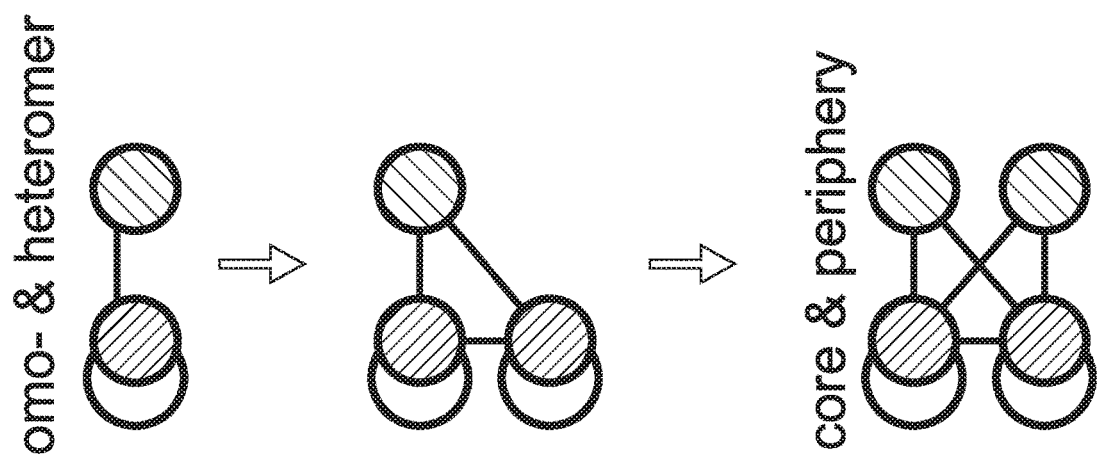
Figure 7C:
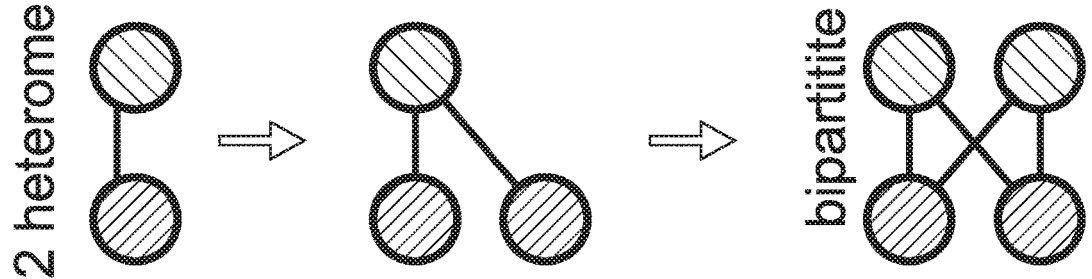

FIGS. 7A-7G are graphs illustrating a simplification of gene duplication and link prediction. FIGS. 7A-7C illustrates, starting from an original link, gene duplication leading to fundamentally different network structures in the three classes, after duplicating both the first (FIG. 7B) and the second node (FIG. 7C). While a link between two heteromers yields a bipartite structure, a link between a homomer and a heteromer leads to a core-periphery structure. Dense clusters or cliques emerge only when starting from a link between two homomers. FIG. 7D illustrates, at the current level of network incompleteness, that not all the resulted links are seen. FIGS. 7E-7G illustrate the top predictions provided by three network based link prediction methods. While both the preferential attachment principle (PA) (FIG. 7E) and the common neighbors method (CN) (FIG. 7F) fail to correctly identify the missing link between two heteromers, the d=3 connectivity principle (FIG. 7G) is expected to work well in all three classes.

G. Degree Difference Between Homomers and Heteromers

As a consequence of both the structural and evolutionary arguments, homomers are expected to have a higher degree compared to heteromers, due to a surplus of links towards similar homomer nodes in dense clusters (local cores and cliques), while heteromer nodes mainly connect to dissimilar nodes only. Indeed, as a group, in all three studied organisms, homomers have a higher degree compared to the rest of the proteins. Due to the degree difference, there is a strong bias towards homomers, leading to ~9% of the links connecting two homomers and 50% of the links connecting two heteromers in the human intercom.

H. Interpretation as a Feature Selection Approach

Figure 8:
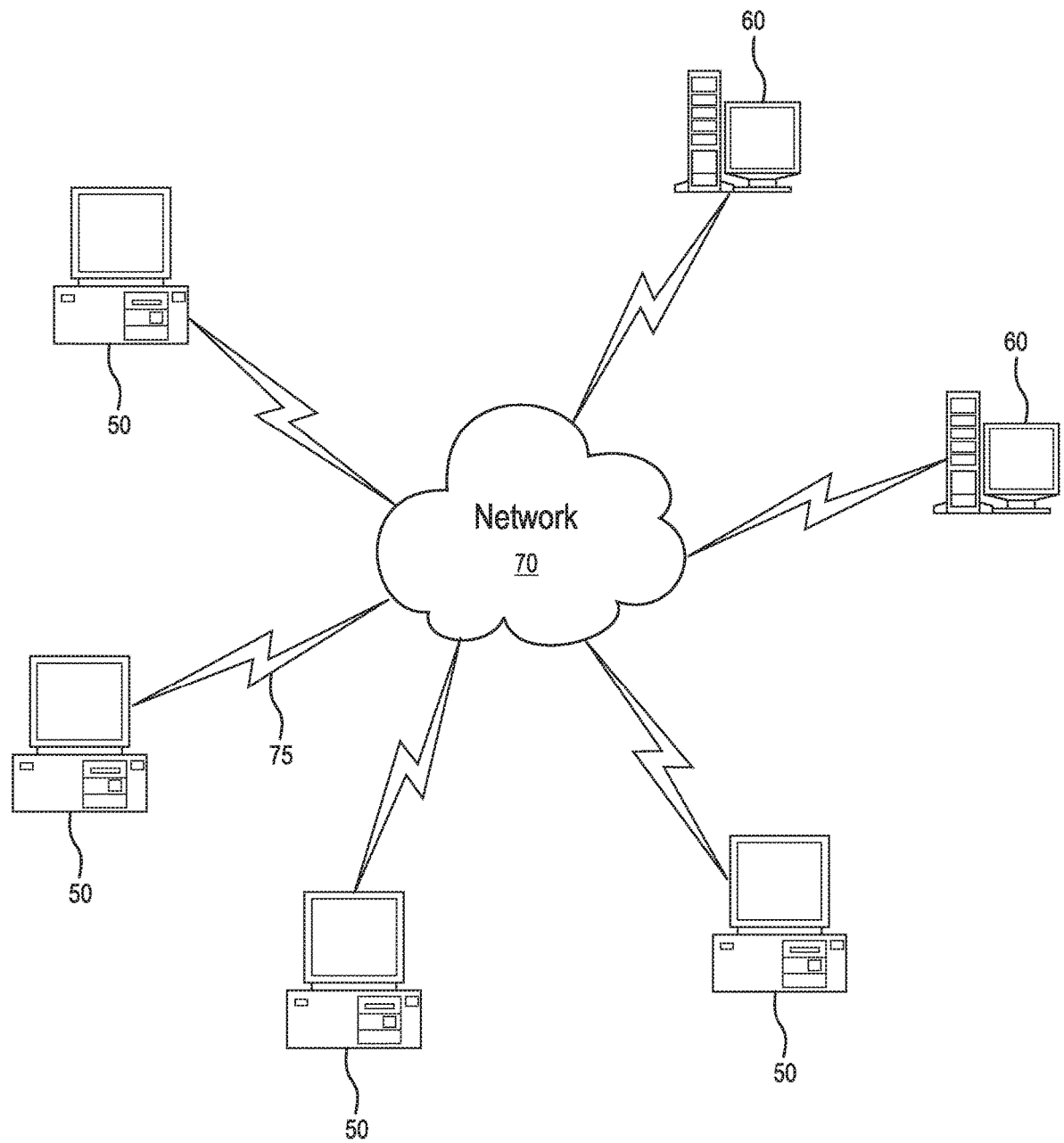
FIG. 8 illustrates a computer network or similar digital processing environment in which embodiments may be implemented.

This can be understood by realizing that the d=3 connectivity can detect all paths at 2-steps as well if at least one of the nodes involved is a homomer, providing an additional step by the self-interaction. d=3 connectivity relies on the same network patterns in the data, while predicting links differently. The key ingredient for both methods is the existence of topologically similar nodes, sharing some of their neighbors. Traditionally, in the TCP it is assumed that such topologically similar nodes should be also connected. On the contrary, a different hypothesis is formulated, stating that a potential neighbor should be topologically similar to the already known neighbors of the node. While this interpretation might hold more generally, even besides biological networks, it is noted, that due to the elegant simplicity of the d=3 connectivity principle, there are other possible alternative interpretations as well Digital Processing Environment FIG. 8 illustrates a computer network or similar digital processing environment in which embodiments of the disclosed systems and methods may be implemented. Client computer(s)/devices 50 and server computer(s) 60 provide processing, storage, and input/output devices executing application programs and the like. The client computer(s)/devices 50 can also be linked through communications network 70 to other computing devices, including other client devices/processes 50 and server computer(s) 60, via communication links 75 (e.g., wired or wireless network connections). The communications network 70 can be part of a remote access network, a global network (e.g., the Internet), a worldwide collection of computers, local area or wide area networks, and gateways that currently use respective protocols (TCP/IP, Bluetooth®, etc.) to communicate with one another. Other electronic device/computer network architectures are suitable.

Figure 9:
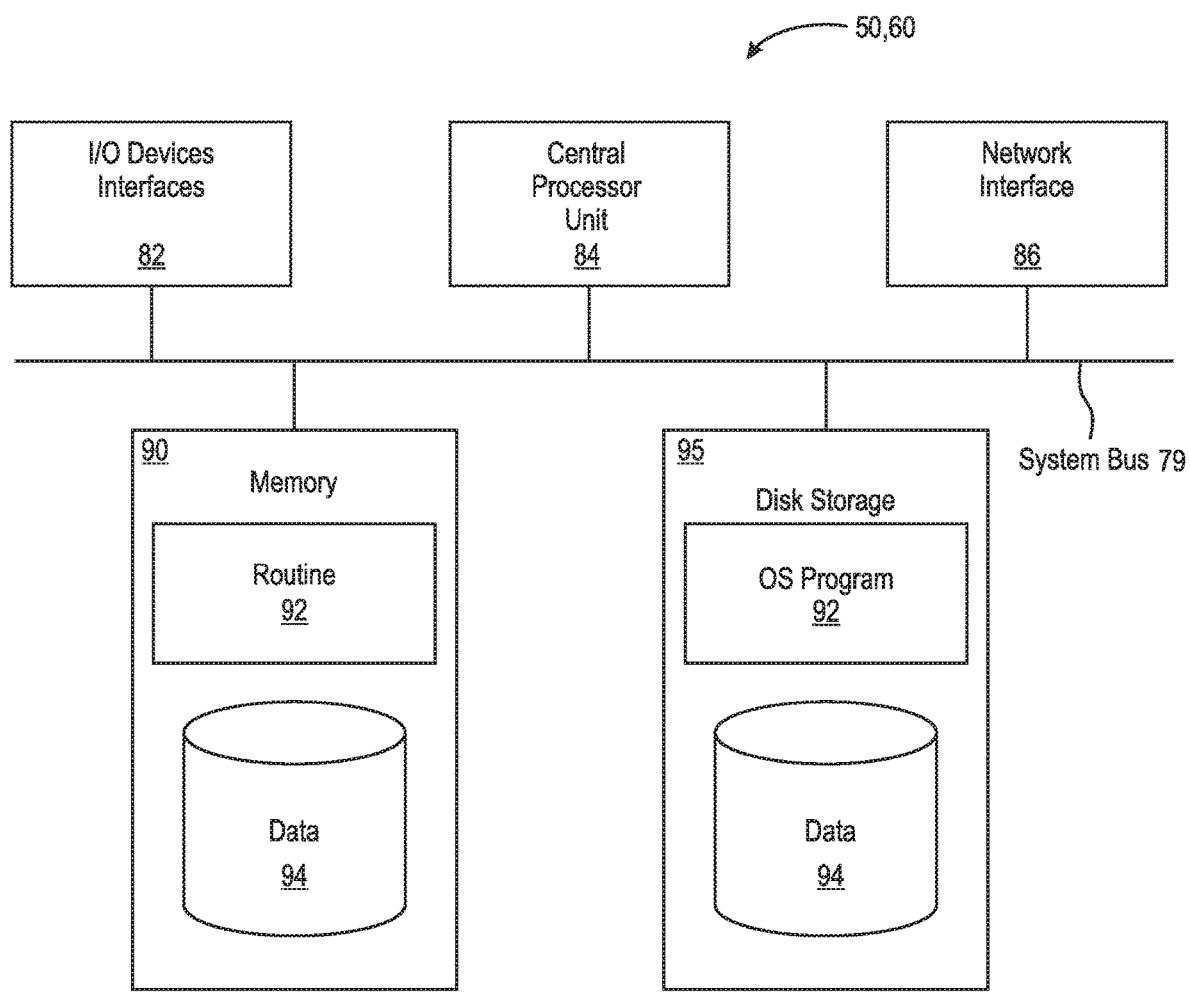
FIG. 9 is a diagram of an example internal structure of a computer in the computer system of FIG. 8.

FIG. 9 is a diagram of an example internal structure of a computer (e.g., client processor/device 50 or server computers 60) in the computer system of FIG. 8. Each computer 50, 60 contains a system bus 79, where a bus is a set of hardware lines used for data transfer among the components of a computer or processing system. The system bus 79 is essentially a shared conduit that connects different elements of a computer system (e.g., processor, disk storage, memory, input/output ports, network ports) that enables the transfer of information between the elements. Attached to the system bus 79 is an I/O device interface 82 for connecting various input and output devices (e.g., keyboard, mouse, displays, printers, speakers) to the computer 50, 60. A network interface 86 allows the computer to connect to various other devices attached to a network (e.g., network 70 of FIG. 8). Memory 90 provides volatile storage for computer software instructions 92 and data 94 used to implement an embodiment of the present invention (e.g., process 100 FIG. 1). Disk storage 95 provides non-volatile storage for computer software instructions 92 and data 94 used to implement an embodiment of the present invention. A central processor unit 84 is also attached to the system bus 79 and provides for the execution of computer instructions. The disk storage 95 or memory 90 can provide storage for a database. Embodiments of a database can include a SQL database, text file, or other organized collection of data.

In one embodiment, the processor routines 92 and data 94 are a computer program product (generally referenced 92), including a non-transitory computer-readable medium (e.g., a removable storage medium such as one or more DVD-ROM's, CD-ROM's, diskettes, tapes) that provides at least a portion of the software instructions for the invention system. The computer program product 92 can be installed by any suitable software installation procedure, as is well known in the art. In another embodiment, at least a portion of the software instructions may also be downloaded over a cable communication and/or wireless connection.

It should be understood that the example embodiments described herein may be implemented in many different ways. In some instances, the various methods, systems, and devices described herein may each be implemented by a physical, virtual, or hybrid general purpose computer. The computer systems 50, 60 may be transformed into machines that execute methods described herein, for example, by loading software instructions into either memory 90 or non-volatile storage 95 for execution by the CPU 84.

Embodiments or aspects thereof may be implemented in the form of hardware, firmware, or software. If implemented in software, the software may be stored on any non-transient computer readable medium that is configured to enable a processor to load the software or subsets of instructions thereof. The processor then executes the instructions and is configured to operate or cause an apparatus to operate in a manner as described herein.

Further, firmware, software, routines, or instructions may be described herein as performing certain actions and/or functions of the data processors. However, it should be appreciated that such descriptions contained herein are merely for convenience and that such actions in fact result from computing devices, processors, controllers, or other devices executing the firmware, software, routines, instructions, etc.

It should be understood that the flow diagrams, block diagrams, and network diagrams may include more or fewer elements, be arranged differently, or be represented differently. But it further should be understood that certain implementations may dictate the block and network diagrams and the number of block and network diagrams illustrating the execution of the embodiments be implemented in a particular way.

Accordingly, further embodiments may also be implemented in a variety of computer architectures, physical, virtual, cloud computers, or some combination thereof, and, thus, the data processors described herein are intended for purposes of illustration only and not as a limitation of the embodiments.

While example embodiments have been particularly shown and described, it will be understood by those skilled in the art that various changes in form and details may be made therein without departing from the scope of the embodiments encompassed by the appended claims.

What is claimed is:

1. A method of identifying missing connections in a complex network, the method comprising, by a processor:
accessing an electronic representation of the network, the network including nodes and links, the nodes representing entities, and the links representing interactions between the entities;
for each pair of nodes in the network not directly connected by a link:
determining a total number of paths connecting the pair of nodes, each path having a length of at least three connections spanning between the pair of nodes in the network; and
calculating a prediction score for the pair of nodes not directly connected in the network, the calculating based on the total number of paths determined as connecting the pair of nodes and having the length of at least three connections;
producing an ordered list of node pairs by ranking the pairs of nodes based on the prediction scores, each pair of nodes of the pairs of nodes not directly connected in the network;
selecting at least a subset of the pairs of nodes based on the ordered list of node pairs, the selected pairs of nodes not directly connected and representing endpoints of missing connections in the network; and
changing the electronic representation by including the missing connections in the network.

2. A method as in claim 1 further comprising communicating the missing connections to at least a portion of entities represented by the selected pairs of nodes.

3. A method as in claim 1 further comprising calculating a statistical significance for each selected pair of nodes by comparing a connection between each pair of nodes to a pool of randomized networks with the same node degrees.

4. A method as in claim 1 further comprising creating connections in the network between each of the selected pairs of nodes.

5. A method as in claim 1 wherein calculating a prediction score for a pair of nodes includes calculating the prediction score based on the number of paths connecting the pair of nodes and a geometric mean of degrees of intermediate nodes between the pair of nodes.

6. A method as in claim 1 further comprising:
collecting data regarding interactions among a plurality of entities; and
creating the electronic representation of the network from the collected data, nodes in the network representing the entities, and connections between nodes in the network representing interactions between corresponding entities.

7. A method as in claim 1 further comprising estimating probabilities of existence of connections between the pairs of nodes by, for each pair of nodes:
performing a leave-one-out analysis, wherein a direct connection between the pair of nodes is left out of the network and each of the pair of nodes is scored in a context of a representation of the remaining network;
adding the leave-one-out score of each of the pair of nodes to the ordered list of node pairs;
estimating a probability of existence of a connection between the pairs of nodes based on the ordered list of node pairs; and
assigning the estimated probability to the pair of nodes.

8. A method as in claim 1 wherein the network is a social network, the nodes of the network representing real-life individuals, and the connections between nodes in the network representing relationships between corresponding individuals; and
wherein the selected pairs of nodes represent relationship recommendations between pairs of corresponding real-life individuals.

9. A method as in claim 8 further comprising:
communicating the relationship recommendations to the individuals represented by the selected pairs of nodes; and
creating a connection between a pair of nodes if at least one of the individuals represented by the nodes verifies a relationship between the individuals.

10. A method as in claim 1 wherein the network is a protein network, the nodes of the network representing real-life human proteins, and the connections between nodes in the network representing functional associations between corresponding proteins; and
wherein the selected pairs of nodes represent new functional relationships between pairs of corresponding proteins.

11. A method as in claim 10 further comprising:
obtaining a protein sequence of a patient; and
applying the protein sequence to the network to determine at least one of a disease afflicting the patient, a drug to use for treating the patient, and a potential reaction by the patient to a drug.

12. A method as in claim 1 wherein the network is a professional network, the nodes of the network representing real-life individuals and businesses, and the connections between nodes in the network representing employment relationships between corresponding individuals and companies; and
wherein the selected pairs of nodes represent employment recommendations between corresponding individuals and companies.

13. A method as in claim 12 further comprising communicating the employment recommendations to the individuals or companies represented by the selected pairs of nodes.

14. A method as in claim 1 wherein the nodes of the network represent real-life individuals and products, and the connections between nodes in the network represent purchases of corresponding products by corresponding individuals; and
wherein the selected pairs of nodes represent purchase recommendations between corresponding individuals and products.

15. A method as in claim 14 further comprising:
communicating the purchase recommendations to individuals represented by the selected pairs of nodes; and
creating a connection between a pair of nodes if the individual represented by the pair of nodes purchases a product represented by the pair of nodes.

16. A system for identifying missing connections in a complex network, the system comprising:
memory storing an electronic representation of a network, the network including:
nodes representing entities; and
links between nodes representing interactions between corresponding entities;
a processor in communication with the memory and configured to:
for each pair of nodes in the network not directly connected:

determine a total number of paths connecting the pair of nodes, each path having a length of at least three connections spanning between the pair of nodes in the network; and calculate a prediction score for the pair of nodes not directly connected in the network, the prediction score calculated based on the total number of paths determined as connecting the pair of nodes and having the length of at least three connections;

produce an ordered list of node pairs by ranking the pairs of nodes based on the prediction scores, each pair of nodes of the pairs of nodes not directly connected in the network;

select at least a subset of the pairs of nodes based on the ordered list of node pairs, the selected pairs of nodes not directly connected and representing endpoints of missing connections in the network; and change the electronic representation of the network by including the missing connections in the network.

17. A system as in claim 16 further comprising an interface by which the processor communicates the missing connections to at least a portion of entities represented by the selected pairs of nodes.

18. A system as in claim 16 wherein the processor is configured to calculate a statistical significance for each selected pair of nodes by comparing a connection between each pair of nodes to a pool of randomized networks with the same node degrees.

19. A system as in claim 16 wherein the processor is configured to create connections in the network between each of the selected pairs of nodes.

20. A system as in claim 16 wherein the processor is configured to calculate a prediction score for a pair of nodes based on the number of paths connecting the pair of nodes and a geometric mean of degrees of intermediate nodes between the pair of nodes.

21. A system as in claim 16 further comprising an interface by which the processor collects data regarding interactions among a plurality of entities; and wherein the processor is configured to create the network from the collected data, nodes in the network representing the entities, and connections between nodes in the network representing interactions between corresponding entities.

22. A system as in claim 16 wherein the processor is configured to estimate probabilities of existence of connections between the pairs of nodes by, for each pair of nodes:

performing a leave-one-out analysis, wherein a direct connection between the pair of nodes is left out of the network and each of the pair of nodes is scored in the remaining network;

adding the leave-one-out score of each of the pair of nodes to the ordered list of node pairs;

estimating a probability of existence of a connection between the pairs of nodes based on the ordered list of node pairs; and assigning the estimated probability to the pair of nodes.

23. A system as in claim 16 wherein the network is a social network, the nodes of the network representing real-life individuals, and the connections between nodes in the network representing relationships between corresponding individuals; and wherein the selected pairs of nodes represent relationship recommendations between pairs of corresponding real-life individuals.

24. A system as in claim 23 further comprising an interface by which the processor communicates the relationship recommendations to the individuals represented by the selected pairs of nodes; and wherein the processor is configured to create a connection in the network between a pair of nodes if at least one of the individuals represented by the nodes verifies a relationships between the individuals.

25. A system as in claim 16 wherein the network is a protein network, the nodes of the network representing real-life human proteins, and the connections between nodes in the network representing functional associations between corresponding proteins; and wherein the selected pairs of nodes represent new functional relationships between pairs of corresponding proteins.

26. A method as in claim 25 further comprising an interface configured to obtain a protein sequence of a patient; and wherein the processor is configured to apply the protein sequence to the network to determine at least one of a disease afflicting the patient, a drug to use for treating the patient, and a potential reaction by the patient to a drug.

27. A system as in claim 16 wherein the network is a professional network, the nodes of the network representing real-life individuals and businesses, and the connections between nodes in the network representing employment relationships between corresponding individuals and companies; and wherein the selected pairs of nodes represent employment recommendations between corresponding individuals and companies.

28. A system as in claim 27 further comprising an interface by which the processor communicates the employment recommendations to the individuals or companies represented by the selected pairs of nodes.

29. A system as in claim 16 wherein the nodes of the network represent real-life individuals and products, and the connections between nodes in the network represent purchases of corresponding products by corresponding individuals; and wherein the selected pairs of nodes represent purchase recommendations between corresponding individuals and products.

30. A system as in claim 29 further comprising an interface by which the processor communicates the purchase recommendations to individuals represented by the selected pairs of nodes; and wherein the processor is configured to create a connection in the network between a pair of nodes if the individual represented by the pair of nodes purchases a product represented by the pair of nodes.

* * * * *